United States Patent
Mateus et al.

(10) Patent No.: US 12,138,069 B2
(45) Date of Patent: Nov. 12, 2024

(54) PLATFORM FOR IDENTIFICATION OF BIOMARKERS USING NAVIGATION TASKS AND TREATMENTS USING NAVIGATION TASKS

(71) Applicant: Akili Interactive Labs, Inc., Boston, MA (US)

(72) Inventors: Ashley Mateus, Cambridge, MA (US); Titiimaea Alailima, Cambridge, MA (US); Jason Johnson, Novato, CA (US); Matthew Omernick, Larkspur, CA (US); Christian Doeller, Trondheim (NO); Hugo Spiers, London (GB); Walter Edward Martucci, Westwood, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 18 days.

(21) Appl. No.: 16/466,745

(22) PCT Filed: Dec. 13, 2017

(86) PCT No.: PCT/US2017/066214
§ 371 (c)(1),
(2) Date: Jun. 5, 2019

(87) PCT Pub. No.: WO2018/112103
PCT Pub. Date: Jun. 21, 2018

(65) Prior Publication Data
US 2019/0343447 A1    Nov. 14, 2019

Related U.S. Application Data

(60) Provisional application No. 62/433,769, filed on Dec. 13, 2016.

(51) Int. Cl.
*A61B 5/00* (2006.01)
*A61B 5/16* (2006.01)
(Continued)

(52) U.S. Cl.
CPC ............ *A61B 5/4088* (2013.01); *A61B 5/168* (2013.01); *A61B 5/4064* (2013.01); *A61B 5/742* (2013.01);
(Continued)

(58) Field of Classification Search
CPC ..... A61B 5/7475; A61B 5/742; A61B 5/4064; A61B 5/168; A61B 5/165; A61B 5/4094;
(Continued)

(56) References Cited

U.S. PATENT DOCUMENTS

2004/0175683 A1    9/2004    Duffy et al.
2008/0118899 A1    5/2008    Sahakian et al.
(Continued)

FOREIGN PATENT DOCUMENTS

JP    2007532219 A    11/2007
JP    2014-508309 A    4/2014
(Continued)

OTHER PUBLICATIONS

Shelton, Amy L., and Timothy P. McNamara. "Orientation and perspective dependence in route and survey learning." Journal of Experimental Psychology: Learning, Memory, and Cognition 30.1 (2004): 158. (Year: 2004).*
(Continued)

*Primary Examiner* — Tse W Chen
*Assistant Examiner* — Michael A Catina
(74) *Attorney, Agent, or Firm* — Gregory Finch; Finch Paolino, LLC

(57) ABSTRACT

A cognitive platform is disclosed that is configured for either or both of assessing or enhancing the cognitive abilities of
(Continued)

an individual based on implementing one or more navigation task(s) in an environment. A first task is rendered that requires the individual to rely on allocentric navigation capabilities to navigate in the environment based on a first set of views of portions of the environment rendered at the user interface. A second task is rendered that requires the individual to rely on egocentric navigation capabilities to navigate in the environment. An indication of a cognitive ability in the individual can be generated based on the difference in the individual's performance at the first task as compared to the second task.

20 Claims, 11 Drawing Sheets

(51) Int. Cl.
*G16H 20/70* (2018.01)
*G16H 50/20* (2018.01)
(52) U.S. Cl.
CPC .......... *A61B 5/7475* (2013.01); *G16H 20/70* (2018.01); *G16H 50/20* (2018.01)
(58) Field of Classification Search
CPC ... A61B 5/4088; A61B 5/4082; A61B 5/4076; A61B 5/4058; G16H 20/70; G16H 20/10; G16H 50/70; G16H 50/50; G16H 50/30; G16H 50/20; G16H 50/00; G16H 40/63; G16H 10/60
See application file for complete search history.

(56) References Cited

U.S. PATENT DOCUMENTS

| | | | | |
|---|---|---|---|---|
| 2008/0280276 | A1* | 11/2008 | Raber | A61B 5/16 434/236 |
| 2012/0108909 | A1 | 5/2012 | Slobounov et al. | |
| 2012/0190968 | A1 | 7/2012 | Raber | |
| 2012/0238936 | A1* | 9/2012 | Hyde | A61B 5/1459 604/8 |
| 2014/0276130 | A1 | 9/2014 | Mirelman et al. | |
| 2014/0315169 | A1* | 10/2014 | Bohbot | G09B 19/00 434/236 |
| 2016/0078780 | A1 | 3/2016 | Alexander et al. | |
| 2016/0125748 | A1 | 5/2016 | Ashford | |
| 2016/0262680 | A1 | 9/2016 | Martucci et al. | |
| 2016/0367837 | A1* | 12/2016 | Moore | A61B 5/4088 |
| 2017/0219611 | A1* | 8/2017 | Ward | G01N 33/6896 |
| 2018/0284138 | A1* | 10/2018 | Yang | G01N 33/54326 |
| 2018/0284141 | A1* | 10/2018 | Ayton | A61B 5/4842 |
| 2019/0330335 | A1* | 10/2019 | Schwabe | A61P 25/28 |
| 2020/0060603 | A1 | 2/2020 | Bower et al. | |
| 2021/0208162 | A1* | 7/2021 | Blumenthal | G01N 33/6893 |

FOREIGN PATENT DOCUMENTS

| | | |
|---|---|---|
| JP | 2014535080 A | 12/2014 |
| WO | 2012064999 A1 | 5/2012 |
| WO | 2013071417 A1 | 5/2013 |
| WO | 2015066037 A1 | 5/2015 |
| WO | 2015179522 A1 | 11/2015 |
| WO | 2016118811 A2 | 7/2016 |
| WO | 2016154682 A1 | 10/2016 |

OTHER PUBLICATIONS

International Search Report, International application No. PCT/US2017/066214. Date of mailing: Mar. 7, 2018. ISA/US, Alexandria, VA.
Written Opinion of the International Searching Authority, International application No. PCT/US2017/066214. Date of mailing: Mar. 7, 2018. ISA/US, Alexandria, VA.
Examination Report, European application No. 17880170.0. Date of mailing: Jul. 6, 2021. European Patent Office, Munich, DE.
Office Action, Korean patent application 10-2019-7020449. English translation. Date of mailing: Jun. 30, 2022. Korean Intellectual Property Office, Daejeon, KR.
Office Action, Australian application No. 2017376455. Date of mailing: Oct. 6, 2022. IP Australia, Phillip, AU.
Office Action, English translation. Japanese application No. 2019-551925. Date of mailing: Jan. 31, 2022. Japan Patent Office, Tokyo, JP.
Office Action, English translation. Japanese application No. 2022-163176. Date of mailing: Jul. 31, 2023. Japan Patent Office, Tokyo, JP.
Office Action, Canadian application No. 3,046,789. Date of mailing: Aug. 24, 2023. Canadian Intellectual Property Office, Gatineau, CA.

\* cited by examiner

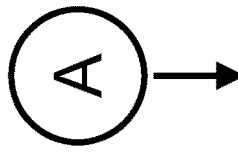

Using the at least one processing unit to: analyze the cData and/or nData to provide a measure of the individual's condition (including cognitive condition), and/or analyze the cData and/or nData to provide a measure of the individual's performance metric for a given type of navigation task (whether the navigation task requires allocentric navigation and/or egocentric navigation), and/or analyze the differences in the individual's performance based on determining the differences between the user's performance at allocentric navigation as compared to the user's performance at egocentric navigation (including based on differences in the cData) and differences in the associated nData, and/or adjust the difficulty level of the navigation task(s) (including CSIs), based on the analysis of the cData (including the measures of the individual's performance determined in the analysis), and/or provide an output or other feedback from the platform product that can be indicative of the individual's performance metric, and/or cognitive abilities (including for screening, monitoring or assessment), and/or response to cognitive treatment, and/or assessed measures of cognition, and/or classify an individual as to amyloid status, and/or presence or expression level of tau proteins, and/or potential efficacy of use of the cognitive platform or platform product when the individual is administered a drug, biologic or other pharmaceutical agent, and/or expected score from the individual's performance of a TOVA® test and/or a RAVLT™ test, and/or classify an individual as to likelihood of onset and/or stage of progression of a condition, and/or to determine a change in dosage of a drug, biologic or other pharmaceutical agent to the individual or to determine an optimal type or combination of drug, biologic or other pharmaceutical agent to the individual.

PLATFORM FOR IDENTIFICATION OF BIOMARKERS USING NAVIGATION TASKS AND TREATMENTS USING NAVIGATION TASKS

CROSS-REFERENCE TO RELATED APPLICATIONS

This application claims priority to and benefit from international patent application number PCT/US2017/066214, filed Dec. 13, 2017, which claims priority to and benefit of U.S. provisional application number 62/433,769, entitled "PLATFORM FOR IDENTIFICATION OF BIOMARKERS USING NAVIGATION TASKS AND TREATMENTS USING NAVIGATION TASKS," filed on Dec. 13, 2016. The entire disclosure of each of these two applications is incorporated herein by reference in its entirety, including drawings.

BACKGROUND OF THE DISCLOSURE

Cognitive dysfunction is one of the characteristics exhibited by individuals with various neurodegenerative conditions such as Alzheimer's disease and Parkinson's disease. Studies show that neurodegenerative conditions can affect areas of the brain such as the caudate nucleus, the hippocampus, and the entorhinal cortex. For example, the early stages of Alzheimer's disease can manifest with memory loss and spatial disorientation. The hippocampus is one of the early regions of the brain to suffer damage resulting in the memory loss and spatial disorientation symptoms. The caudate nucleus is implicated in motor and spatial functions. Physiological techniques and other technology used to measure the state of these regions of the brain can be costly, inefficient, and time-consuming.

SUMMARY OF THE DISCLOSURE

In view of the foregoing, apparatus, systems and methods are provided for quantifying aspects of cognition (including cognitive abilities). The indication of cognitive abilities of an individual can provide insight into the relative health or strength of about portions of the brain of the individual. In certain configurations, the example apparatus, systems and methods can be implemented for enhancing certain cognitive abilities of the individual.

Example systems, methods, and apparatus herein can be implemented to generate an assessment of one or more cognitive skills in an individual. An example includes rendering a first task that requires an individual to rely on allocentric navigation capabilities to navigate in an environment based on a first set of views of portions of the environment rendered at the user interface, and generating a first set of data based on measurements of a first set of one or more parameters associated with allocentric navigation performed by the individual in response to the first task. The example method also includes rendering a second task that requires the individual to rely on egocentric navigation capabilities to navigate in the environment based on a second set of views of portions of the environment rendered at the user interface, and generating a second set of data based on measurements of a second set of one or more parameters associated with egocentric navigation performed by the individual in response to the second task. The example systems, methods, and apparatus are configured to analyze the first set of data and the second set of data and to generate an indication of a cognitive ability in the individual based on a difference in the individual's performance at the first task as compared to the individual's performance at the second task, at least in part by determining a difference between the first set of data and the second set of data.

Example systems, methods, and apparatus herein can be implemented to enhance one or more cognitive skills in an individual via implementation of two or more iterations of the tasks to be performed. The example systems, methods, and apparatus are configured to iteratively perform, in a series of at least two iterations: rendering tasks that require an individual to navigate in an environment based on one or more views of at least a portion of the environment rendered at the user interface, in which the one or more views are updated as the individual navigates the environment, receiving navigation commands from the individual, controlling navigation in the environment based on the received navigation commands, measuring a first set of one or more parameters that provide information indicating the individual's allocentric navigation capabilities in performing the one or more tasks based on one or more first views of at least a portion of the environment, and generating a first set of data having information about the measurements of the first set of one or more parameters, measuring a second set of one or more parameters that provide information indicating the individual's egocentric navigation capabilities in performing the tasks based on one or more second views of at least a portion of the environment, and generating a second set of data having information about the measurements of the second set of one or more parameters, and analyzing at least a portion of the first set of data and the second set of data. One or more of the requirements of a given task, the difficulty level of the task, or the type of the task rendered in the second iteration or a later iteration can be configured based at least in part on the analysis of at least one of the first set of data and the second set of data associated with one or more parameters measured in one or more previous iterations. The systems, methods, and apparatus are configured to generate an indication of the cognitive ability in the individual based on a difference in the individual's performance at the tasks derived from the analyses of the first sets of data and the second sets of data associated with the responses to the tasks in at least some of the iterations.

The details of one or more of the above aspects and implementations are set forth in the accompanying drawings and the description below. Other features, aspects, and advantages will become apparent from the description, the drawings, and the claims.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIGS. 4A-4D show flowcharts of example methods, according to the principles herein.

DETAILED DESCRIPTION

Figure 1A:
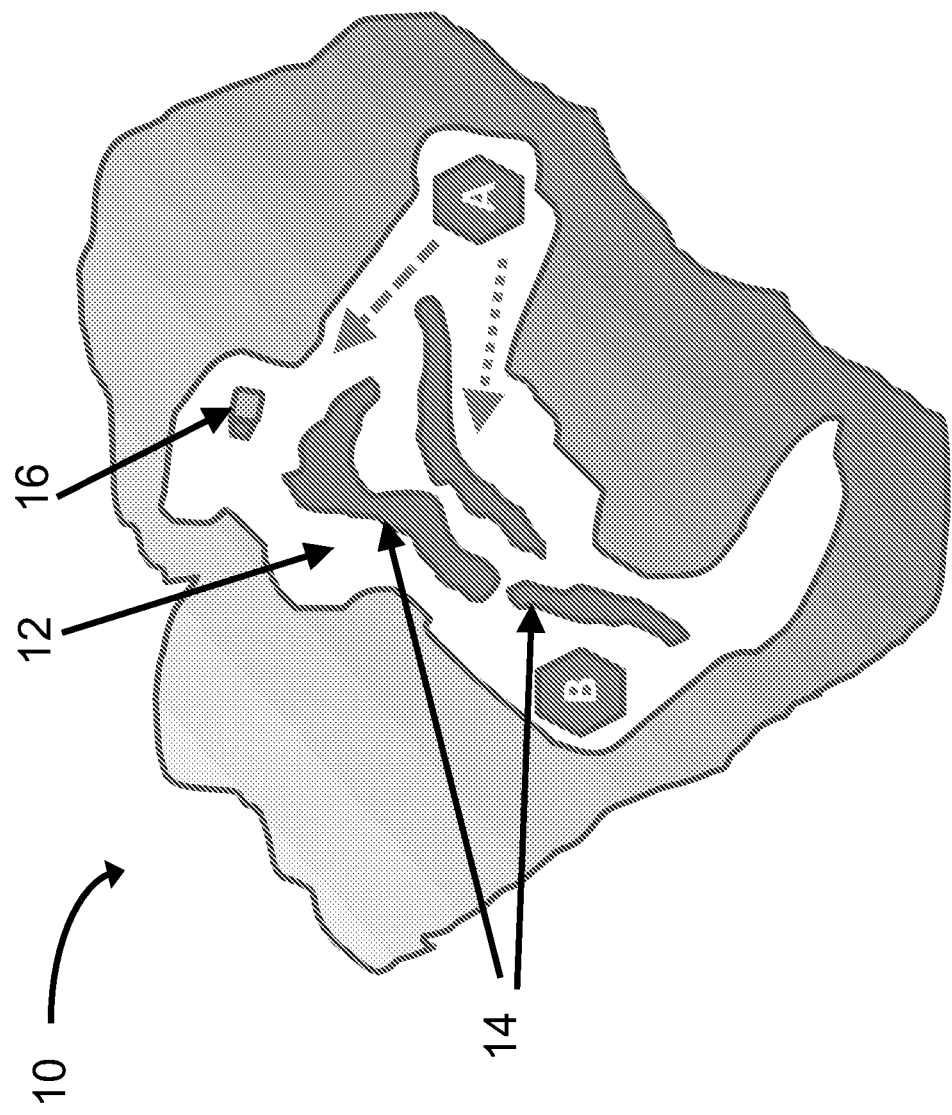
FIGS. 1A-1C show non-limiting examples of computerized renderings of courses for presentation of navigation tasks, according to the principles herein.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems comprising a cognitive platform configured for implementing one or more navigation task(s). The cognitive platform also can be configured for coupling with one or more other types of measurement components, and for analyzing data indicative of at least one measurement of the one or more other types of components. As non-limiting examples, the cognitive platform can be configured for cognitive training and/or for clinical purposes. According to the principles herein, the cognitive platform may be integrated with one or more physiological or monitoring components and/or cognitive testing components.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, the term "including" means including but not limited to. The term "based on" means based at least in part on.

The example platform products and cognitive platforms according to the principles described herein can be applicable to many different types of conditions, such as but not limited to depression, attention deficit hyperactivity disorder (ADHD), Alzheimer's disease, dementia, Parkinson's disease, Huntington's disease, Cushing's disease, schizophrenia, or other condition.

The ability of an individual to navigate from an initial point to a desired location in a real or virtual environment (such as but not limited to a virtual town or small maze), including the ability to formulate and/or execute a strategy to find the way from the initial point to the goal location, can depend at least in part on use of a number of different areas of the brain. These areas are the caudate nucleus region of the brain, the entorhinal cortex and hippocampal regions of the brain. See, e.g., Hafting et al., "Microstructure of a spatial map in the entorhinal cortex", *Nature*, vol. 436, issue 7052, pp. 801-806 (2005); Bohbot et al., "Gray matter differences correlate with spontaneous strategies in a human virtual navigation task," *Journal of Neuroscience*, vol. 27, issue 38, pp. 10078-10083 (2007).

In an example where an individual performs a navigation task that activates the caudate nucleus region of the brain, the individual is learning a rigid set of stimulus-response type associations referred to as dependent stimulus-response navigation strategies. A non-limiting example of a dependent stimulus-response navigation strategy is, e.g., see the tree and turn right.

In an example where an individual performs a navigation task by learning the spatial relationship between the landmarks in an environment, the individual is relying on hippocampal dependent spatial navigation strategies, via activating the hippocampal region of the brain. An individual relying on the entorhinal cortex region of the brain for navigation forms a directionally-oriented topographically organized neural map of the spatial environment, which includes translational and directional information. That map is anchored to external landmarks, but can persist in the absence of those external landmarks. The contextual specificity of hippocampal representations suggests that during encoding, the hippocampus associates output from a generalized, path-integration-based coordinate system with landmarks or other features specific to a particular environment. Through back projections to the superficial layers of the entorhinal cortex, associations stored in the hippocampus may reset the path integrator as errors accumulate during exploration of an environment. Anchoring the output of the path integrator to external reference points stored in the hippocampus or other cortical areas of the brain may enable alignment of entorhinal maps from one trial to the next, even when the points of departure are different.

An individual may navigate through a given environment using an allocentric form of navigation and/or an egocentric form of navigation. In implementing a given type of navigation strategy, an individual uses differing portions of the brain.

As used herein, "allocentric" refers to a form of navigation where an individual identifies places in the environment independent of the individual's perspective (or direction) and ongoing behavior. In allocentric navigation, an individual centers their attention and actions on other items in the environment rather than their own perspective. Parameters that can be measured to indicate allocentric navigation include measures of an individual's judgment about the horizontal distance between two points (e.g., their relative spatial position as measured based on distances relative to other objects in the environment), an individual's ability to plot a novel course through a previously traversed (and therefore known) environment (i.e., a course that differs in at least one parameter from a previous course through the environment), and an individual's ability to spatially transform (e.g. rotate, translate, or scale) three or more memorized positions in an environment arranged to cover two or more dimensions.

Areas of the brain such as the entorhinal cortex and hippocampus are used for allocentric navigation. The allocentric navigation can involve spatial grid navigation and formulation of a memory of how various places are located on the spatial grid and relative to each other. The hippocampus is implicated in both spatial memory and navigation. The medial entorhinal cortex contributes to spatial information processing.

As used herein, "egocentric" refers to a form of navigation where points in the environment are defined in terms of their distance and direction from the individual. Parameters that can be measured to indicate egocentric navigation include the direction and speed of the individual's movements relative to the environment. In an egocentric navigation system, positions in the environment are defined relative to the individual, such that movement of the individual is accompanied by an updating of the individual's perspective representation of a given point.

Areas of the brain such as the caudate nucleus are used in egocentric navigation. The egocentric navigation can involve memory of landmarks and turn-by-turn directions. The caudate nucleus is implicated in motor and spatial functions.

Measures of the relative strength of each area of the brain can inform the cognitive condition of an individual. According to the principles herein, analysis of data indicative of these measurement parameters can be used to detect the very early signs of conditions such as but not limited to Alzheimer's disease.

In an example system, method, and apparatus can be configured to generate a scoring output as an indication of a relative health or strength of the caudate nucleus region of the brain of the individual relative to the entorhinal cortex and hippocampal regions of the brain of the individual. The scoring output can be computed based on the analysis of the data collected from measurements as an individual performs a navigation task that relies on allocentric navigation capabilities as compared to the data collected from measurements as an individual performs a navigation task that relies on egocentric navigation capabilities.

In an example system, method, and apparatus can be configured to generate a scoring output as an indication of a likelihood of onset of a neurodegenerative condition of the individual, or a stage of progression of the neurodegenerative condition, based at least in part on the analysis of first set of data and the second set of data, based on the analysis of the data collected from measurements as an individual performs a navigation task that relies on allocentric navigation capabilities as compared to the data collected from measurements as an individual performs a navigation task that relies on egocentric navigation capabilities.

The example system, method, and apparatus can be configured to transmit the scoring output to the individual and/or display the scoring output on a user interface.

For example, the early stages of Alzheimer's disease (AD) can manifest with memory loss and spatial disorientation. The hippocampus is one of the early regions of the brain to suffer damage resulting in the memory loss and spatial disorientation symptoms. Kunz et al., Science, vol. 350, issue 6259, p. 430 (2015), also proposed that Alzheimer's disease pathology starts in the entorhinal cortex, with the disease likely impairing local neural correlates of spatial navigation such as grid cells. Analysis of measurement data indicative of the individual's performance at navigation tasks, such as data indicative of the type of navigation and/or the degree of success at the navigation task, can provide an indication of the relative strength of the hippocampus and entorhinal cortex. For example, the analysis of data indicative of the individual's performance of the navigation tasks can be used to provide a measure of entorhinal and/or hippocampal dysfunction in individuals, thereby providing a measure of the likelihood of onset of Alzheimer's disease and/or the degree of progression of the disease.

As non-limiting examples, Alzheimer's disease, Parkinson's disease, vascular dementia, and mild cognitive impairment potentially have a greater effect on the hippocampal and entorhinal regions of the brain.

As non-limiting examples, attention deficit hyperactivity disorder, Huntington's disease, obsessive-compulsive disorder, and depression (major depressive disorder) potentially have a greater effect on the caudate nucleus region of the brain.

Example systems, methods, and apparatus herein can be implemented to collect data indicative of measures of the relative strength of areas of the brain implicated in navigation. Data indicative of the individual's performance based on the type of navigation (i.e., allocentric navigation vs egocentric navigation) and/or the degree of success at navigation can be used to provide an indication of the relative strength of each area of the brain of the individual.

In implementing an allocentric navigation strategy, an individual is relying more on the activation of the hippocampal and the entorhinal cortex regions of the brain (needing the context of one or more features to guide navigation strategy). In an example, the individual's performance on a task requiring allocentric navigation skills could be an indicator of the level of activation of the caudate nucleus region of the brain, such that poorer values of performance measure(s) could indicate poorer activation of the hippocampal and/or the entorhinal cortex regions of the brain. For example, the entorhinal cortex region of the brain can become more efficient once a navigation strategy is processed by the hippocampal region.

In implementing an egocentric navigation strategy, an individual is relying more on the activation of the caudate nucleus region of the brain (navigation learning strategy based on using self as the point of reference). In an example where an individual's performance of the task requiring egocentric navigation is relatively poor, this could indicate that the individual takes fewer cues from the environment. Where the individual is less able to take cues from the environment, the individual cannot use this mechanism to learn. The individual's performance on a task requiring egocentric navigation skills could be an indicator of the level of activation of the caudate nucleus region of the brain, such that poorer values of performance measure(s) could indicate poorer activation of the caudate nucleus region of the brain.

Example systems, methods, and apparatus herein can be implemented to generate an assessment of one or more cognitive skills in an individual. An example includes rendering a first task that requires an individual to rely on allocentric navigation capabilities to navigate in an environment based on a first set of views of portions of the environment rendered at the user interface, and generating a first set of data based on measurements of a first set of one or more parameters associated with allocentric navigation performed by the individual in response to the first task. The example method also includes rendering a second task that requires the individual to rely on egocentric navigation capabilities to navigate in the environment based on a second set of views of portions of the environment rendered at the user interface, and generating a second set of data based on measurements of a second set of one or more parameters associated with egocentric navigation performed by the individual in response to the second task. The example systems, methods, and apparatus are configured to analyze the first set of data and the second set of data and to generate an indication of a cognitive ability in the individual based on a difference in the individual's performance at the first task as compared to the individual's performance at the second task, at least in part by determining a difference between the first set of data and the second set of data.

For example, differences in the first and second data set might indicate poorer numerical values of parameters measured. As non-limiting examples, the parameters can be one or more of a measure of a navigation speed relative to the environment, an orientation relative to the environment, a velocity relative to the environment, a choice of navigation strategy, a measure of a wait or delay period or a period of inaction during performance of the navigation task, a time interval to complete a course of the navigation task, or a degree of optimization of a navigation path through a course.

In an example implementation, the system, method and apparatus can be configured to generate assessments that provide indications of the potential for onset of and/or progression or stage of a neurodegenerative condition that affects one region of the brain (e.g., caudate nucleus region) versus another (hippocampal and/or entorhinal cortex region). The analysis of the data indicating the relative strength of the individual at performing a navigation task based on allocentric capabilities versus egocentric capabilities can help to indicate what type of neurodegenerative condition is potentially affecting the individual, to what degree the individual is affected, and how much damage there might be to a given region of the individual's brain. For example, Alzheimer's disease, Parkinson's disease, vascular dementia, and mild cognitive impairment potentially have a greater effect on the hippocampal and entorhinal regions of the brain, and attention deficit hyperactivity disorder, Huntington's disease, obsessive-compulsive disorder, and depression (major depressive disorder) potentially have a greater effect on the caudate nucleus region of the brain.

In an example implementation, the system, method and apparatus can be configured to generate assessments that provide indications of the regions of the brain that may not be strengthened (or potentially re-built) as a result of the potential for onset of and/or progression or stage of a neurodegenerative condition that affects one region of the brain (e.g., caudate nucleus region) versus another (hippocampal and/or entorhinal cortex region). Accordingly, one or more of the systems, methods, and apparatus herein can be configured to enhance the cognitive skills of the individual based on enhancing the other region of the brain which can be strengthened (or potentially re-built) to help the individual navigate and recognize visual cues.

Example systems, methods, and apparatus herein can be implemented to enhance one or more cognitive skills in an individual via implementation of two or more iterations of the tasks to be performed. The example systems, methods, and apparatus are configured to iteratively perform, in a series of at least two iterations: rendering tasks that require an individual to navigate in an environment based on one or more views of at least a portion of the environment rendered at the user interface, in which the one or more views are updated as the individual navigates the environment, receiving navigation commands from the individual, controlling navigation in the environment based on the received navigation commands, measuring a first set of one or more parameters that provide information indicating the individual's allocentric navigation capabilities in performing the one or more tasks based on one or more first views of at least a portion of the environment, and generating a first set of data having information about the measurements of the first set of one or more parameters, measuring a second set of one or more parameters that provide information indicating the individual's egocentric navigation capabilities in performing the tasks based on one or more second views of at least a portion of the environment, and generating a second set of data having information about the measurements of the second set of one or more parameters, and analyzing at least a portion of the first set of data and the second set of data. One or more of the requirements of a given task, the difficulty level of the task, or the type of the task rendered in the second iteration or a later iteration can be configured based at least in part on the analysis of at least one of the first set of data and the second set of data associated with one or more parameters measured in one or more previous iterations. The systems, methods, and apparatus are configured to generate an indication of the cognitive ability in the individual based on a difference in the individual's performance at the tasks derived from the analyses of the first sets of data and the second sets of data associated with the responses to the tasks in at least some of the iterations.

In some examples, the difficulty level of the tasks rendered in one or more of iterations (e.g., in the second or a later iteration) can be modified based at least in part on the analysis of one or both of the first sets of data or the second set of data. The difficulty level can be increased by modifying one or more of a required navigation speed relative to the environment, a complexity of the turns and number of rewards of seek goals on the course, a restriction on orientation of the perspectives rendered to the individual relative to the environment, a required minimum velocity required of the individual relative to the environment, a restriction in the number or choice of navigation strategy, a limit to the wait or delay period or a period of inaction during performance of the navigation task, a reduction in the time interval to complete a course of the navigation task, or a requirement of an increased degree of optimization of a navigation path through a course.

The example system, method and apparatus can be configured to enhance the individual's capabilities at either or both of the egocentric navigation and allocentric navigation. In an example where the individual's capabilities at allocentric navigation is affected, such as but not limited to due to a neurodegenerative condition that affects the hippocampal and/or entorhinal cortex region of the brain, the example system, method and apparatus can be configured to strengthen the individual's capabilities at egocentric navigation. In an example where the individual's capabilities at egocentric navigation is affected, such as but not limited to due to a neurodegenerative condition that affects the caudate nucleus region of the brain, the example system, method and apparatus can be configured to strengthen the individual's capabilities at allocentric navigation. As a result, an individual that is being affected by the neurodegenerative condition may be able to regain certain of the capabilities diminished by the neurodegenerative condition.

For example, for an individual that no longer recognizes faces or people well, the systems, methods, and apparatus can be used to strengthen the capabilities of the individual to navigate the environment without relying on visual cues, social cues, or other capabilities that can be gained from enhancing the other unaffected regions of the brain.

As non-limiting examples, "navigation" refers to wayfinding, path-plotting, seek or search and recovery, direction-giving, or other similar types of tasks.

The instant disclosure is directed to computer-implemented devices formed as example platform products configured to implement software and/or other processor-executable instructions for the purpose of measuring data indicative of a user's performance at one or more navigation tasks, to provide a user performance metric. As non-limiting examples, performance metrics can include data indicative of an individual's navigation speed, orientation, velocity, choice of navigation strategy, wait or delay period, or other period of inaction, prior to continuing in a given direction of a course or changing direction, time interval to complete a course, frequency or number of times of referral to an aerial or elevated view of a landscape (including as a map), including values of any of these parameters as a function of time. As another non-limiting example, the performance metrics can include a measure of the degree of optimization of the path navigated by the individual through the course, such as though determining the shortest path or near-shortest path through the course.

The example performance metric can be used to derive an assessment of a user's cognitive abilities and/or to measure a user's response to a cognitive treatment, and/or to provide data or other quantitative indicia of a user's condition (including cognitive condition). In non-limiting examples, the performance metric can be used to derive measures of the relative strength of each area of the brain. Non-limiting example cognitive platforms or platform products according to the principles herein can be configured to classify an individual as to relative health or strength of regions of the brain such as but not limited to the caudate nucleus region of the brain and the entorhinal cortex and hippocampal regions of the brain, and/or potential efficacy of use of the cognitive platform or platform product when the individual is administered a drug, biologic or other pharmaceutical agent, based on the data collected from the individual's interaction with the cognitive platform or platform product and/or metrics computed based on the analysis (and associated computations) of that data. Yet other non-limiting example cognitive platforms or platform products according to the principles herein can be configured to classify an individual as to likelihood of onset and/or stage of progression of a cognitive condition, based on the data collected from the individual's interaction with the cognitive platform or platform product and/or metrics computed based on the analysis (and associated computations) of that data. The cognitive condition can be, but is not limited to, depression, attention deficit hyperactivity disorder (ADHD), Alzheimer's disease, dementia, Parkinson's disease, Huntington's disease, Cushing's disease, or schizophrenia.

Any classification of an individual as to likelihood of onset and/or stage of progression of a cognitive condition according to the principles herein can be transmitted as a signal to a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in dosage (such as but not limited to an amount, concentration, or dose titration) of a drug, biologic or other pharmaceutical agent to the individual or to determine an optimal type or combination of drug, biologic or other pharmaceutical agent to the individual.

In any example herein, the platform product or cognitive platform can be configured as any combination of a medical device platform, a monitoring device platform, a screening device platform, or other device platform.

The instant disclosure is also directed to example systems that include platform products and cognitive platforms that are configured for coupling with one or more physiological or monitoring component and/or cognitive testing component. In some examples, the systems include platform products and cognitive platforms that are integrated with the one or more other physiological or monitoring component and/or cognitive testing component. In other examples, the systems include platform products and cognitive platforms that are separately housed from and configured for communicating with the one or more physiological or monitoring component and/or cognitive testing component, to receive data indicative of measurements made using such one or more components.

As used herein, the term "cData" refers to data collected from measures of an interaction of a user with a computer-implemented device formed as a platform product.

As used herein, the term "nData" refers to other types of data that can be collected according to the principles herein. Any component used to provide nData is referred to herein as a nData component.

In any example herein, the cData and/or nData can be collected in real-time.

In non-limiting examples, the nData can be collected from measurements using one or more physiological or monitoring components and/or cognitive testing components. In any example herein, the one or more physiological components are configured for performing physiological measurements. The physiological measurements provide quantitative measurement data of physiological parameters and/or data that can be used for visualization of physiological structure and/or functions.

As a non-limiting example, nData can be collected from measurements of types of protein and/or conformation of proteins in the tissue or fluid (including blood) of an individual and/or in tissue or fluid (including blood) collected from the individual. In some examples, the tissue and or fluid can be in or taken from the individual's brain. In other examples, the measurement of the conformation of the proteins can provide an indication of amyloid formation (e.g., whether the proteins are forming aggregates).

As a non-limiting example, the nData can be collected from measurements of beta amyloid, cystatin, alpha-synuclein, huntingtin protein, and/or tau proteins. In some examples, the nData can be collected from measurements of other types of proteins that may be implicated in the onset and/or progression of a neurodegenerative condition, such as but not limited to Alzheimer's disease, dementia, Parkinson's disease, Huntington's disease, Cushing's disease, or schizophrenia. For example, tau proteins are deposited in the hippocampal area of the brain first in Alzheimer's disease.

In a non-limiting example, nData can be a classification or grouping that can be assigned to an individual based on measurement data from the one or more physiological or monitoring components and/or cognitive testing components. For example, an individual can be classified in as to amyloid status of amyloid positive (A+) or amyloid negative (A−).

In some examples, the nData can be an identification of a type of biologic, drug or other pharmaceutical agent administered or to be administered to an individual, and/or data collected from measurements of a level of the biologic, drug or other pharmaceutical agent in the tissue or fluid (including blood) of an individual, whether the measurement is made in situ or tissue or fluid (including blood) using collected from the individual. Non-limiting examples of a biologic, drug or other pharmaceutical agent applicable to any example described herein include methylphenidate (MPH), scopolamine, donepezil hydrochloride, rivastigmine tartrate, memantine HCl, solanezumab, aducanumab, and crenezumab.

It is understood that reference to "drug" herein encompasses a drug, a biologic and/or other pharmaceutical agent.

In other non-limiting examples, nData can include any data that can be used to characterize an individual's status, such as but not limited to age, gender or other similar data.

In any example herein, the data (including cData and nData) is collected with the individual's consent.

In any example herein, the one or more physiological components can include any means of measuring physical characteristics of the body and nervous system, including electrical activity, heart rate, blood flow, and oxygenation levels, to provide the nData. This can include camera-based heart rate detection, measurement of galvanic skin response, blood pressure measurement, electroencephalogram, electrocardiogram, magnetic resonance imaging, near-infrared spectroscopy, and/or pupil dilation measures, to provide the nData.

Other examples of physiological measurements to provide nData include, but are not limited to, the measurement of body temperature, heart or other cardiac-related functioning using an electrocardiograph (ECG), electrical activity using an electroencephalogram (EEG), event-related potentials (ERPs), functional magnetic resonance imaging (fMRI), blood pressure, electrical potential at a portion of the skin, galvanic skin response (GSR), magneto-encephalogram (MEG), eye-tracking device or other optical detection device including processing units programmed to determine degree of pupillary dilation, functional near-infrared spectroscopy (fNIRS), and/or a positron emission tomography (PET) scanner. An EEG-fMRI or MEG-fMRI measurement allows for simultaneous acquisition of electrophysiology (EEG/MEG) nData and hemodynamic (fMRI) nData.

In any example herein, the cognitive platform and systems including the cognitive platform can be configured to present computerized navigation tasks and platform interactions that inform cognitive assessment (including screening or monitoring) or deliver a treatment.

Figure 1B:
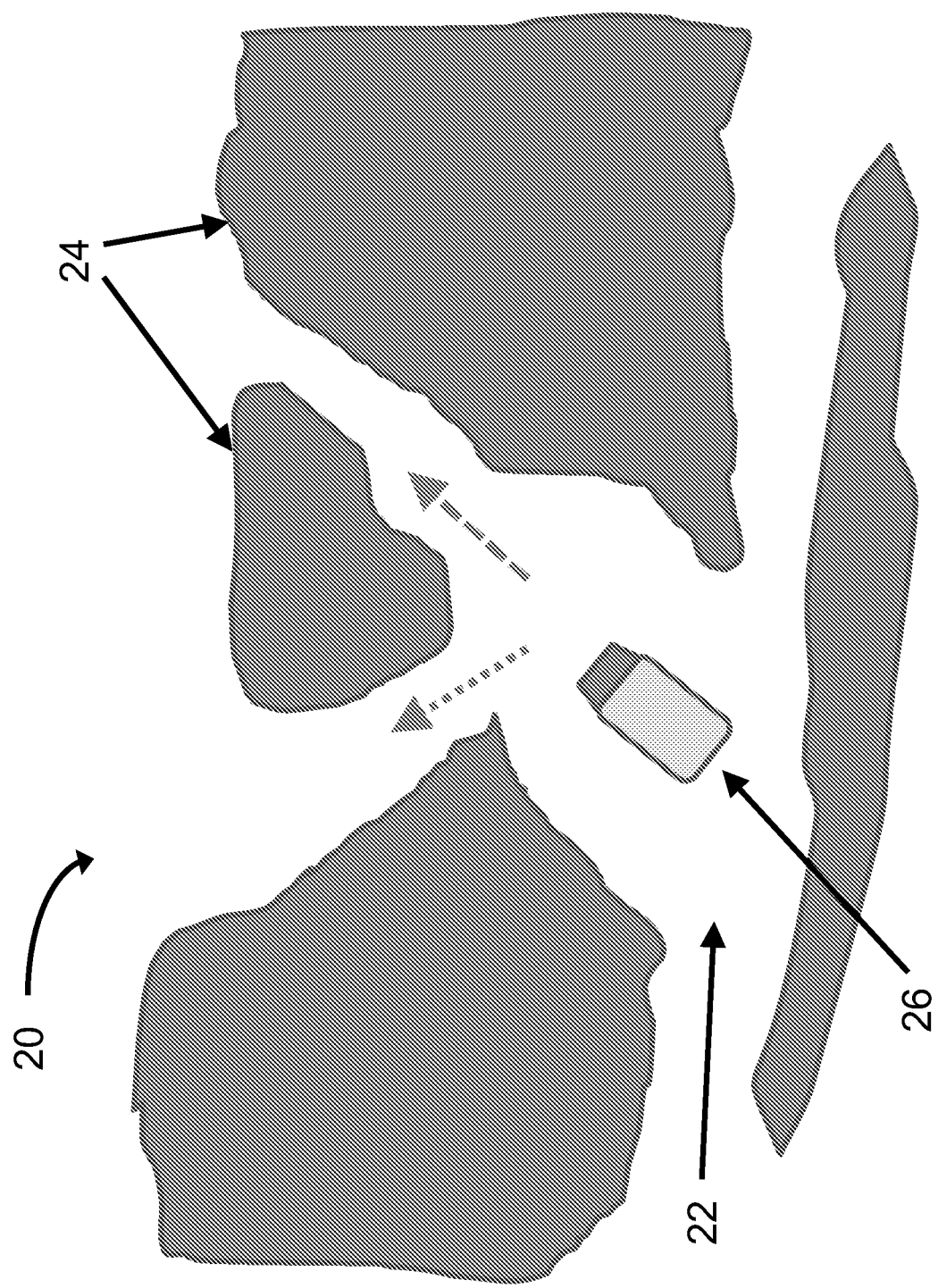

FIGS. 1A and 1B show non-limiting examples of computerized renderings of courses that present navigation tasks.

FIG. 1A shows a non-limiting example of a computerized rendering of a course that can be used to present a navigation task according to the principles herein. In this example, the computing device is configured to present an elevated, overhead view of a landscape 10 that includes one or more internal course 12 and obstacles 14. In this example, portions of the course 12 are configured to include pathways and passageways that allow traversal of an avatar or other guidable element 16. The navigation task requires an individual to formulate a pathway about the strategically positioned obstacles 14 from an initial point ("A") to at least one target location ("B"). The computing device can be configured to present instructions to the individual to navigate the course 12. The computing device also can be configured to provide an individual with an input device or other type of control element that allows the individual to traverse the course 12, including specifying and/or controlling one or more of the speed of movement, orientation, velocity, choice of navigation strategy, the wait or delay period, or other period of inaction, prior to continuing in a given direction of a course or changing direction, time interval to complete a course, and/or frequency or number of times of referral to an aerial or elevated view of a landscape (including as a map), including values of any of these parameters as a function of time. As another non-limiting example, the performance metrics can include a measure of the degree of optimization of the path navigated by the individual through the course, such as though determining the shortest path or near-shortest path through the course.

The computing device can be configured to collect data indicative of the performance metric that quantifies the navigation strategy employed by the individual from the initial point ("A") to reach one or more target points ("B"). For example, the computing device can be configured to collect data indicative of the individual's decision to proceed from the initial point ("A") along the dashed line or the dotted line, the speed of movement, the orientation of the avatar or other guidable element 16, among other measures. In the various examples, performance metrics that can be measured using the computing device can include data indicative of the speed of movement, orientation, velocity, choice of navigation strategy, wait or delay period, or other period of inaction, prior to continuing in a given direction of a course or changing direction, time interval to complete a course, and/or frequency or number of times of referral to an aerial or elevated view of a landscape (including as a map), including values of any of these parameters as a function of time. As another non-limiting example, the performance metrics can include a measure of the degree of optimization of the path navigated by the individual through the course, such as though determining the shortest path or near-shortest path through the course.

In an example, the course 12 may include one or more target points $B_i$ (i=1, 2, 3, . . . ) that the individual is instructed to locate in traversing the course 12. In this example, the performance metric may include a scoring based on the number of targets located and/or the time taken to locate the targets. In a non-limiting example, the individual may be instructed to navigate the course 12 such that the multiple targets are located in a specified sequence. In this example, the performance metric may include a scoring based on the number of targets located in sequence and/or the time taken to complete the sequence.

FIG. 1B shows a non-limiting example of another computerized rendering that can be used to present a navigation task according to the principles herein. In this example, the computing device is configured to present a more localized overhead view of a selected portion of a landscape 20 that the individual is required to navigate. Portions of the course 22 are defined by obstacles 24, and are configured to allow traversal of an avatar or other guidable element 26. In this example, the view of the landscape is sufficiently localized that an individual may be required to make selections or decisions on strategy to traverse the course without benefit of an aerial view of the entire course or a significant portion of the course. The computing device can be configured to collect data indicative of the individual's decision to proceed along the dashed line or the dotted line, and/or the speed of movement, and/or the orientation of the avatar or other guidable element 26, among other measures. In this example, performance metrics that can be measured using the computing device relative to the localized landscape can include data indicative of one or more of the speed of movement, orientation, velocity, choice of navigation strategy, wait or delay period, or other period of inaction, prior to continuing in a given direction of a course or changing direction, time interval to complete a course, and/or frequency or number of times of referral to an aerial or elevated view of a landscape (including as a map), including values of any of these parameters as a function of time. As another non-limiting example, the performance metrics can include a measure of the degree of optimization of the path navigated by the individual through the course, such as though determining the shortest path or near-shortest path through the course.

In an example, the course 22 may include one or more target points $B_i$ (i=1, 2, 3, . . . ) that the individual is instructed to locate in traversing the course 22. In this example, the performance metric may include a scoring based on the number of targets located and/or the time taken to locate the targets. In a non-limiting example, the individual may be instructed to navigate the course 122 such that the multiple targets are located in a specified sequence. In this example, the performance metric may include a scoring based on the number of targets located in sequence and/or the time taken to complete the sequence.

In an example, a computing device can be configured to present an individual with the capability of changing, in at least one instance in a session, from a wider aerial view (such as but not limited to the perspective shown in FIG. 1A) to a more localized view (such as but not limited to the perspective shown in FIG. 1B).

As a non-limiting example implementation, an individual may be presented with an aerial view such as shown in FIG. 1A to obtain an overview of the course, but then be required to navigate the course from the more localized perspective shown in FIG. 1B. In this example, an individual may be required to rely on allocentric navigate capabilities, to navigate the course by making selections and decisions from more localized views similar to that shown in FIG. 1B based on the memory the individual forms from the wider aerial view of FIG. 1A.

Figure 1C:
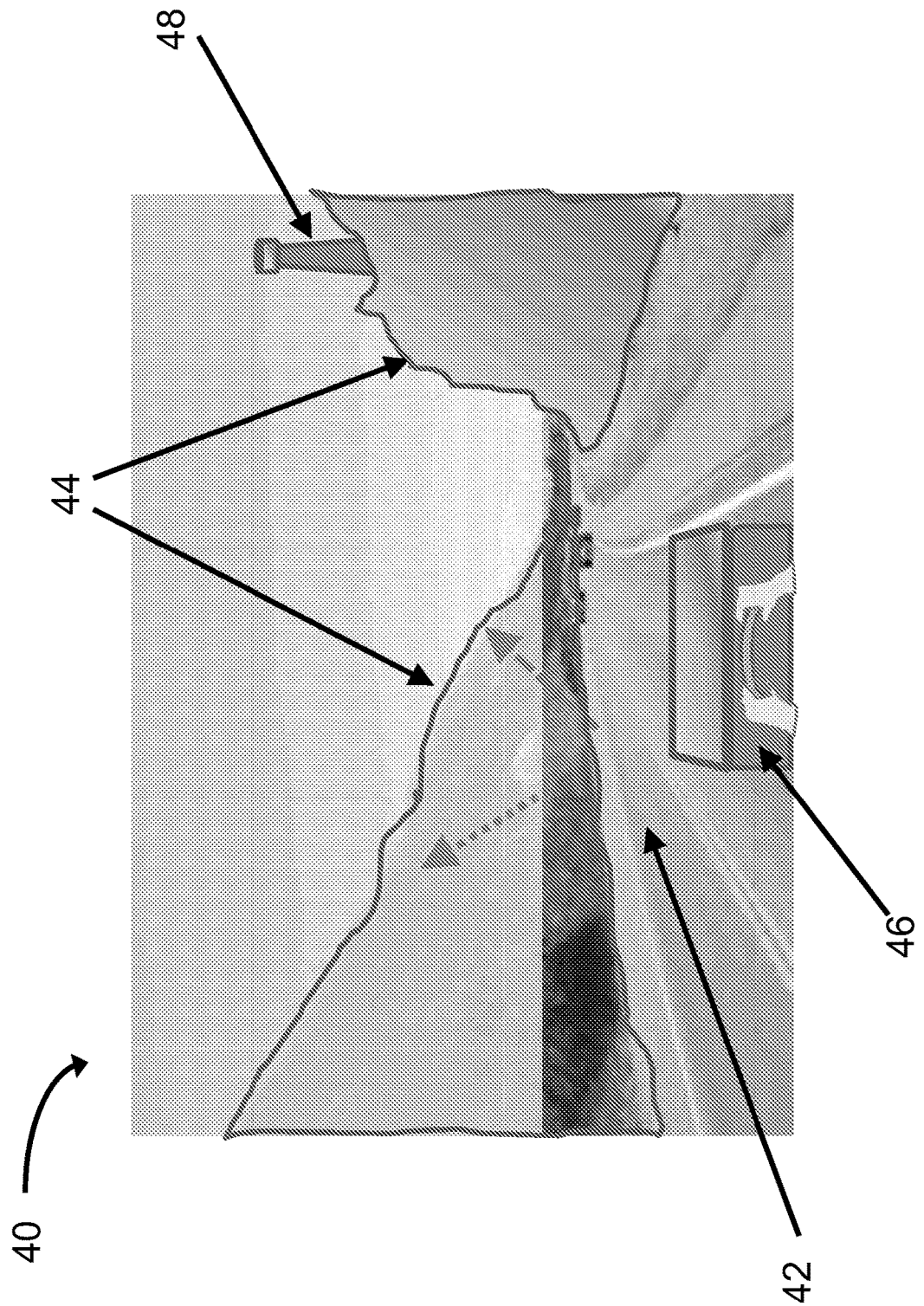

FIG. 1C shows a non-limiting example of another computerized rendering that can be used to present a navigation task according to the principles herein. In this example, the computing device is configured to present a view of a selected portion of a landscape 40 that the individual is required to navigate, but from the perspective of the avatar or other guidable element 46. Portions of the course 42 are defined by obstacles 44, and are configured to allow traversal of the avatar or other guidable element 46. In this example, the individual may be required to make selections or decisions on strategy to traverse the course without benefit of an aerial view of the entire course or a significant portion of the course. The computing device can be configured to collect data indicative of the individual's decision to proceed along the dashed line or the dotted line, and/or the speed of movement, and/or the orientation of the avatar or other guidable element 46, among other measures. In this example, performance metrics that can be measured using the computing device relative to the localized landscape can include data indicative of one or more of the speed of movement, orientation, velocity, choice of navigation strategy, wait or delay period, or other period of inaction, prior to continuing in a given direction of a course or changing direction, time interval to complete a course, and/or frequency or number of times of referral to an aerial or elevated view of a landscape (including as a map), including values of any of these parameters as a function of time. As another non-limiting example, the performance metrics can include a measure of the degree of optimization of the path navigated by the individual through the course, such as though determining the shortest path or near-shortest path through the course.

As a non-limiting example implementation, an individual may be presented with a perspective view such as shown in FIG. 1C, and be presented with a set of instructions to assist in navigating the course. In this example, an individual may be required to rely on egocentric navigate capabilities, to navigate the course by making selections and decisions based on position of the avatar or guidable element 46 at a given point or based on one or more landmarks in the landscape. As a non-limiting example of a landmark (element 48 shown in FIG. 1C), a computerized rendering of a tower can be positioned relative to an obstacle 44, such that an individual may use the landmark 48 as a guide in formulating a navigation strategy. In this example, the individual may use the landmark 48 in a form of egocentric navigation.

In an example, the course 42 may include one or more target points $B_i$ (i=1, 2, 3, . . . ) that the individual is instructed to locate in traversing the course 42. In this example, the performance metric may include a scoring based on the number of targets located and/or the time taken to locate the targets. In a non-limiting example, the individual may be instructed to navigate the course 42 such that the multiple targets are located in a specified sequence. In this example, the performance metric may include a scoring based on the number of targets located in sequence and/or the time taken to complete the sequence.

In any example herein, the course through an example landscape may be include land-based solid surfaces (including paved road, dirt road, or other types of ground surfaces) and/or waterways.

In any example, the landscape may instead be waterways defined by obstacles other than land-based obstacles, such as but not limited to buoys or other anchored float, reefs, jetties or other applicable type of obstacle.

In any example herein, one or more navigation tasks can be computer-implemented as computerized elements which require position-specific and/or motion-specific responses from the user. In non-limiting examples, the user response to the navigation task(s) can be recorded using an input device of the cognitive platform. Non-limiting examples of such input devices can include a touch, swipe or other gesture relative to a user interface or image capture device (such as but not limited to a keyboard, a touch-screen or other pressure sensitive screen, or a camera), including any form of graphical user interface configured for recording a user interaction. In other non-limiting examples, the user response recorded using the cognitive platform for the navigation task(s) can include user actions that cause changes in a position, orientation, or movement of a computing device including the cognitive platform. Such changes in a position, orientation, or movement of a computing device can be recorded using an input device disposed in or otherwise coupled to the computing device, such as but not limited to a sensor. Non-limiting examples of sensors include a joystick, a mouse, a motion sensor, a position sensor, a pressure sensor, and/or an image capture device (such as but not limited to a camera).

In an example implementation, the computer device is configured (such as using at least one specially-programmed processing unit) to cause the cognitive platform to present to a user one or more different type of navigation tasks during a specified time frame.

In some examples, the time frame can be of any time interval at a resolution of up to about 30 seconds, about 1 minute, about 5 minutes, about 10 minutes, about 20 minutes, or longer.

In some examples, the platform product or cognitive platform can be configured to collect data indicative of a reaction time of a user's response relative to the time of presentation of the navigation tasks.

In some examples, the difficulty level of the navigation task can be changed by increasing the intricacy of the convolutions or number or density of misdirection portions of the course, reducing the time required to complete the course, increase the complexity of the target location requirements. In any example herein, a misdirection portion in a course causes the avatar or other guidable element to move off course, reach a portion of an obstacle that cannot be traversed, and/or not load to a desired target.

In a non-limiting example implementation, the example platform product herein may be formed as, be based on, or be integrated with, an AKILI® platform product (also referred to herein as an "APP") by Akili Interactive Labs, Inc., Boston, MA.

As used herein, the term "computerized stimuli or interaction" or "CSI" refers to a computerized element that is presented to a user to facilitate the user's performance of the navigation task.

For example, the navigation task can be presented to a user by rendering a graphical user interface to present the computerized stimuli or interaction (CSI) or other interactive elements. Description of use of (and analysis of data from) one or more CSIs in the various examples herein also encompasses use of (and analysis of data from) navigation tasks comprising the one or more CSIs in those examples.

In an example where the computing device is configured to present at least one navigation task comprising at least one CSI, the at least one navigation task and at least one CSI can be rendered using the at least one graphical user interface. The computing device can be configured to measure data indicative of the responses as the user performs the at least one navigation task and to measure data indicative of the interactions with the at least one CSI. In some examples, the rendered at least one graphical user interface can be configured to measure data indicative of the responses as the user performs the at least one navigation task and to measure data indicative of the interactions with the at least one CSI.

In any example according to the principles herein, the CSIs may be reward items or other interaction elements located at the one or more target points $B_i$ (i=1, 2, 3, . . . ) that the individual is instructed to locate in traversing a course. In this example, the performance metric may include a scoring based on the number of reward items or other interaction elements located by the individual and/or the time taken to locate the reward items or other interaction elements. Non-limiting examples of reward items or other interaction elements include coins, stars, faces (including faces having variations in emotional expression) or other dynamic element.

In a non-limiting example, the graphical user interface can be configured such that the CSI computerized element(s) are active, and may require at least one response from a user, such that the graphical user interface is configured to measure data indicative of the type or degree of interaction of the user with the platform product. In another example, the graphical user interface can be configured such that the CSI computerized element(s) are a passive and are presented to the user using the at least one graphical user interface but may not require a response from the user. In this example, the at least one graphical user interface can be configured to exclude the recorded response of an interaction of the user, to apply a weighting factor to the data indicative of the response (e.g., to weight the response to lower or higher values), or to measure data indicative of the response of the user with the platform product as a measure of a misdirected response of the user (e.g., to issue a notification or other feedback to the user of the misdirected response).

In an example, the platform product can be configured as a processor-implemented system, method or apparatus that includes and at least one processing unit. In an example, the at least one processing unit can be programmed to render at least one graphical user interface to present the navigation task(s) and one or more CSI to the user for interaction. The at least one processing unit can be programmed to cause a component of the program product to receive data indicative of the navigation and/or at least one user response based on the user interaction with the CSI (such as but not limited to cData), including responses provided using the input device. The at least one processing unit also can be programmed to: analyze the cData to provide a measure of the individual's performance metric for a given type of navigation task (whether allocentric or egocentric), and/or analyze the differences in the individual's performance based on determining the differences between the user's performance at allocentric navigation a compared to the user's performance at egocentric navigation (including based on differences in the cData), and/or adjust the difficulty level of the navigation task(s) (including CSIs), based on the analysis of the cData (including the measures of the individual's performance determined in the analysis), and/or provide an output or other feedback from the platform product that can be indicative of the individual's performance metric, and/or cognitive abilities (including for screening, monitoring or assessment), and/or response to cognitive treatment, and/or assessed measures of cognition. In non-limiting examples, the at least one processing unit also can be programmed to classify an individual as to amyloid status, and/or presence or expression level of tau proteins, and/or potential efficacy of use of the cognitive platform or platform product when the individual is administered a drug, biologic or other pharmaceutical agent, and/or expected score from the individual's performance of a TOVA® test and/or a RAVLT™ test, based on the cData collected from the individual's interaction with the cognitive platform or platform product and/or metrics computed based on the analysis (and associated computations) of that cData. In non-limiting examples, the at least one processing unit also can be programmed to classify an individual as to likelihood of onset and/or stage of progression of a condition, based on the cData collected from the individual's interaction with the cognitive platform or platform product and/or metrics computed based on the analysis (and associated computations) of that cData. The condition can be, but is not limited to, depression, attention deficit hyperactivity disorder (ADHD), Alzheimer's disease, dementia, Parkinson's disease, Huntington's disease, Cushing's disease, schizophrenia, or other condition.

In other examples, the platform product can be configured as a processor-implemented system, method or apparatus that includes a display component, an input device, and the at least one processing unit. The at least one processing unit can be programmed to render at least one graphical user interface, for display at the display component, to present the navigation task(s) (including the CSI) to the user for interaction.

Non-limiting examples of an input device include a touch-screen, or other pressure-sensitive or touch-sensitive surface, a motion sensor, a position sensor, a pressure sensor, and/or an image capture device (such as but not limited to a camera).

The analysis of the individual's performance may include using the computing device to compute percent accuracy at the navigation task, number of hits and/or misses at locating the target(s) during a session or from a previously completed session. Other indicia that can be used to compute performance measures is the amount time the individual takes to respond after the presentation of a task (e.g., as a targeting stimulus). Other indicia can include, but are not limited to, reaction time, response variance, number of correct hits, omission errors, false alarms, learning rate, spatial deviance, subjective ratings, and/or performance threshold, etc.

In a non-limiting example, the computerized element includes at least one element to indicate positive feedback to a user. Each element can include an auditory signal and/or a visual signal emitted to the user that indicates success at a navigation task or other platform interaction element, i.e., that the user responses at the platform product has exceeded a threshold success measure on a navigation task.

In a non-limiting example, the computerized element includes at least one element to indicate negative feedback to a user. Each element can include an auditory signal and/or a visual signal emitted to the user that indicates failure at a navigation task, i.e., that the user responses at the platform product has not met a threshold success measure on a navigation task.

In a non-limiting example, the computerized element includes at least one element for messaging, i.e., a communication to the user that is different from positive feedback or negative feedback.

In a non-limiting example, the computerized element includes at least one element for indicating a CSI that is a reward. A reward computer element can be a computer generated feature that is delivered to a user to promote user satisfaction with the navigation task and as a result, increase positive user interaction (and hence enjoyment of the user experience).

According to the principles herein, the term "cognition" or "cognitive" refers to the mental action or process of acquiring knowledge and understanding through thought, experience, and the senses. This includes, but is not limited to, psychological concepts/domains such as, executive function, memory, perception, attention, emotion, motor control, and interference processing. An example computer-implemented device according to the principles herein can be configured to collect data indicative of user interaction with a platform product, and to compute metrics that quantify user performance. The quantifiers of user performance can be used to provide measures of cognition (for cognitive assessment) or to provide measures of status or progress of a cognitive treatment.

According to the principles herein, the term "treatment" or "treat" refers to any manipulation of CSI in a platform product (including in the form of an APP) that results in a measurable improvement of the abilities of a user, such as but not limited to improvements related to cognition, a user's mood, emotional state, and/or level of engagement or attention to the cognitive platform. The degree or level of improvement can be quantified based on user performance measures as describe herein. In an example, the term "treatment" may also refer to a therapy.

According to the principles herein, the term "session" refers to a discrete time period, with a clear start and finish, during which a user interacts with a platform product to receive assessment or treatment from the platform product (including in the form of an APP).

According to the principles herein, the term "assessment" refers to at least one session of user interaction with CSIs or other feature or element of a platform product. The data collected from one or more assessments performed by a user using a platform product (including in the form of an APP) can be used as to derive measures or other quantifiers of cognition, or other aspects of a user's abilities.

According to the principles herein, the term "cognitive load" refers to the amount of mental resources that a user may need to expend to complete a task. This term also can be used to refer to the challenge or difficulty level of a navigation task.

In an example, the platform product can be configured as a processor-implemented system, method or apparatus that includes and at least one processing unit. In an example, the at least one processing unit can be programmed to render at least one graphical user interface to present the navigation task(s) and one or more CSI to the user for interaction. The at least one processing unit can be programmed to cause a component of the program product to receive data indicative of the performance of the navigation task and/or at least one user response based on the user interaction with the CSI (such as but not limited to cData), including responses provided using the input device. The platform product also can be configured to receive nData indicative of measurements made before, during, and/or after the user interacts with the cognitive platform (including nData from measurements of physiological or monitoring components and/or cognitive testing components). The at least one processing unit also can be programmed to: analyze the cData and/or nData to provide a measure of the individual's condition (including cognitive condition), analyze the cData and/or nData to provide a measure of the individual's performance metric for a given type of navigation task (whether the navigation task requires allocentric navigation and/or egocentric navigation), and/or analyze the differences in the individual's performance based on determining the differences between the user's performance at allocentric navigation as compared to the user's performance at egocentric navigation (including based on differences in the cData) and differences in the associated nData. The at least one processing unit also can be programmed to: adjust the difficulty level of the navigation task(s) (including CSIs), based on the analysis of the cData (including the measures of the individual's performance determined in the analysis), and/or provide an output or other feedback from the platform product that can be indicative of the individual's performance metric, and/or cognitive abilities (including for screening, monitoring or assessment), and/or response to cognitive treatment, and/or assessed measures of cognition. In non-limiting examples, the at least one processing unit also can be programmed to classify an individual as to amyloid status, and/or presence or expression level of tau proteins, and/or potential efficacy of use of the cognitive platform or platform product when the individual is administered a drug, biologic or other pharmaceutical agent, and/or expected score from the individual's performance of a TOVA® test and/or a RAVLT™ test, based on nData and the cData collected from the individual's interaction with the cognitive platform or platform product and/or metrics computed based on the analysis (and associated computations) of that cData and the nData. In non-limiting examples, the at least one processing unit also can be programmed to classify an individual as to likelihood of onset and/or stage of progression of a condition, based on nData and the cData collected from the individual's interaction with the cognitive platform or platform product and/or metrics computed based on the analysis (and associated computations) of that cData and the nData. The condition can be, but is not limited to, depression, attention deficit hyperactivity disorder (ADHD), Alzheimer's disease, dementia, Parkinson's disease, Huntington's disease, Cushing's disease, schizophrenia or other condition.

In an example, the feedback from the differences in the individual's performance based on determining the differences between the measures of the user's first type and second type of responses and the nData can be used as an input in the cognitive platform that indicates real-time performance of the individual during one or more session(s). The data of the feedback can be used to as an input to a computation component of the computing device to determine a degree of adjustment that the cognitive platform makes to a difficulty level of the first task and/or the first interference that the user interacts within the same ongoing session and/or within a subsequently-performed session.

An example system, method, and apparatus according to the principles herein includes a platform product (including using an APP) that is configured to identify the type of navigation strategy that is being used by a participant.

An example system, method, and apparatus according to the principles herein includes a platform product (including using an APP) that is configured to determine the relative strength of each navigation skill (whether egocentric navigation or allocentric navigation) for a given individual or set or population of individuals.

For example, if the weak areas in a disease population (such as but not limited to Alzheimer's disease, recurrent major depression, Parkinson's Disease, Huntington's Disease, ADHD) are strengthened with training on a cognitive platform configured to present a certain type of navigation task (e.g. allocentric navigation to strengthen the hippocampus as compared to egocentric navigation to strengthen the caudate nucleus), there could be transfer of benefit to the disease symptoms of the individual(s) related to that respective brain area (such as but not limited to navigation abilities and potentially memory related to the hippocampus, working memory, learning, and response selection related to the caudate nucleus).

As the hippocampus constructs and maintains a cognitive map of a given environment, and retrieves previously constructed maps (including landscape or waterways maps) when the individual is presented with a new environment that appears similar to a previously visited an environment, measurements of interest include speed and accuracy of learning a new map, employing an old map, and differentiating between maps that appear similar.

An example system, method, and apparatus according to the principles herein includes a platform product (including using an APP) that is configured to evaluate the navigation strategy being used by an individual or group of individuals.

For example, the platform product (including using an APP) may be configured to present a user with conflicting information, such as but not limited to, egocentric landmark cues that would suggest different path choices than the simultaneously available allocentric boundary and path integration information. The example platform product can be configured to measure data indicative of cues that dictate the path choices of the individual. This can provide an indication of the individual's strategy preference. The indication of the individual's strategy preference can be correlated with relative capabilities in respectively associated areas of the individual's brain (i.e., areas of the brain governing allocentric navigation versus egocentric navigation).

An example system, method, and apparatus according to the principles herein includes a platform product (including using an APP) that is configured to measure the change in navigation performance of an individual as measured by metrics such as but not limited to the distance traveled to reach one or more targets (e.g., where a shorter distance is used as a metric of better performance) or by the amount of time taken to reach the one or more target (e.g., faster time is used as a metric of better performance), where the navigation task(s) is set in similar virtual environments, but with varying levels of landmarks available for navigating or varying the salience of the landmarks (such as but not limited to making landmarks look more similar (i.e., fewer distinctions), smaller, less distinct color from the background, etc). The example platform product (including using an APP) can be configured to perform an analysis to compare these measurements. If the performance metrics indicate that individual's performance gets worse as the number of landmarks decreases, the individual can be classified as more likely to be using egocentric navigation.

In a non-limiting example, the platform product (including using an APP) can be configured to analyze the measures of the individual's performance across the environments, and analyze how the individual's performance changes with the number of landmarks. This outcome from the analysis of the individual's performance can be compared between neurotypical individuals and/or individuals of known disease populations, to determine if the performance profile is different between the individual and the neurotypical individuals and/or individuals of known disease populations.

An example system, method, and apparatus according to the principles herein includes a platform product (including using an APP) that is configured to measure the navigation performance of an individual as measured by metrics such as but not limited to the distance traveled to reach one or more targets (e.g., where a shorter distance is used as a metric of better performance) or by the amount of time taken to reach the one or more target (e.g., faster time is used as a metric of better performance), where the navigation task(s) is set in a virtual environment that is changing as the individual is traversing the environment. As non-limiting examples of changes, the landmark features can be changing (e.g., tree changing color in a forest), the landmarks may be duplicated (e.g., first landmark is a pink tree and more pink trees appear over time), the landmarks are changing locations relative to the target(s) and/or other landmarks, the salience of landmarks are changing (e.g., they are getting darker and/or the colors become less clear), or the ability to use landmarks changes (e.g., it becomes foggy and landmarks are less visible). The example platform product (including using an APP) can be configured to perform an analysis to compare performance metrics measured in the changing environment relative to a static environment, to identify the specific state of areas of the brain of an individual (e.g., whether these areas are similar to or different from that of a given population, or show any benefit or deficit) and the individual's specific navigation strategy preferences.

An example system, method, and apparatus according to the principles herein includes a platform product (including using an APP) that is configured to measure the navigation performance (of an individual as measured by metrics such as but not limited to the distance traveled to reach one or more targets (e.g., where a shorter distance is used as a metric of better performance) or by the amount of time taken to reach the one or more target (e.g., faster time is used as a metric of better performance), where the navigation task(s) in a previously explored virtual environment where the starting point and/or target(s) require traversal of the environment via paths to which the individual is not previously exposed (and thus were not previously learned). In one example implementation, this can be achieved by configuring the platform product to introduce new obstacles in the way of previously displayed (and thereby known) paths of the course. In another example implementation, this can be achieved by configuring the platform product to place intermediary target(s) at locations that are outside of previously traveled paths of the course. In another example implementation, this can be achieved by configuring the platform product to introduce a completely different path that never intersects with the previously traversed (and thereby learned) paths of the course. The example platform product (including using an APP) can be configured to perform an analysis to determine an individual's ability to navigate in this condition as a better indication of tendency towards allocentric navigation than possible with repeated wayfinding tasks in previously known paths.

An example system, method, and apparatus according to the principles herein includes a platform product (including using an APP) that is configured to measure the navigation performance of an individual as measured by metrics such as but not limited to the distance traveled to reach one or more targets (e.g., where a shorter distance is used as a metric of better performance) or by the amount of time taken to reach the one or more target (e.g., faster time is used as a metric of better performance), where the navigation task(s) is in a previously explored virtual environment that is being traversed one or more additional times, potentially after varying levels of delay between repeated trials in that environment. In this example, the platform product can be configured to present other activities to the individual into the intervening periods, to introduce cognitive interference. In this example, the platform product can be configured to present other navigation activities that introduce spatial-memory-specific interference, whereas non-navigation activities may be used to introduce other types of interference. The example platform product (including using an APP) can be configured to perform an analysis to compare the measurements from the previously explored virtual environment before and after the intervening periods to determine measures of the improvement in the individual's performance over subsequent same-environment trials as an indication of the rate of learning. The example platform product (including using an APP) can be configured to perform an analysis to compare the measurements from the previously explored virtual environment before and after the intervening periods to determine measures of the changes in performance between to same-environment trials, and the degree of correlation with the amount of delay between to repetitions to determine the effect of time delay on an individual's ability at maintenance of spatial memories. The example platform product (including using an APP) can be configured to perform an analysis to compare the measurements from the previously explored virtual environment before and after the intervening periods to determine measures contrasting trial-to-trial performance changes, where the intervening activities that introduced different types of interference can be used to provide a measure of how much of the interference effects are due specifically to any given type of interference (e.g. spatial memory interference) rather than just task-switching. The example platform product (including using an APP) can be configured to perform an analysis to compare the measurements from the previously explored virtual environment before and after the intervening periods to provide an indicator of the efficiency of spatial memory retrieval based on an analysis of the measures of the impact of spatial memory interference.

An example system, method, and apparatus according to the principles herein includes a platform product (including using an APP) that is configured to measure the navigation performance (of an individual (as measured by the distance traveled to reach one or more targets (e.g., where a shorter distance is used as a metric of better performance) or by the amount of time taken to reach the one or more target (e.g., faster time is used as a metric of better performance), where the navigation task(s) is in a virtual environment that is spatially analogous to a previously explored environment, but without the same visual cues. For example, the analogous environment may be the same as the original environment but with little or no lighting. Alternatively, the analogous environment may be on a different vertical plane (e.g. on a different floor of the same building, in the sky, or underground). Similarly, the analogous environment may have the same shape, but be on a different scale than the previously explored environment. The example platform product (including using an APP) can be configured to perform an analysis to determine a measure of the individual's ability to navigate in this condition as an indication of allocentric navigation.

An example system, method, and apparatus according to the principles herein includes a platform product (including using an APP) that is configured to present an individual with a virtual environment that is spatially analogous to a previously explored environment, without the same visual cues, but not informing the individual which of multiple possible previous environments is the source. The example platform product (including using an APP) can be configured to measure the individual's ability to determine the actual source environment, either directly by prompting the individual to make a choice after sufficient exploration (as a non-limiting example, with performance measures of correctness of choice and the exploration time required to arrive at that choice) or indirectly by prompting the individual to perform movements and/or actions within the environment that correspond to locations within the source environment (as a non-limiting example, with performance measures of distance traveled to one or more targets (e.g., where a shorter distance is used as a metric of better performance) or by the amount of time taken to reach the one or more target (e.g., faster time is used as a metric of better performance). The example platform product (including using an APP) can be configured to perform an analysis to determine a measure of the individual's ability to determine the source environment as an indication of ability to flexibly manipulate multiple cognitive maps under uncertainty, a specific form of active spatial memory interference.

An example system, method, and apparatus according to the principles herein includes a platform product (including using an APP) that is configured to apply a predictive model to data indicative of the cognitive ability in the individual. The predictive model can be configured based on computational techniques and machine learning tools, such as but not limited to linear/logistic regression, principal component analysis, generalized linear mixed models, random decision forests, support vector machines, or artificial neural networks, to the cData and nData to create composite variables or profiles that are more sensitive than each measurement alone for detecting disease or assessing cognitive health.

An example system, method, and apparatus according to the principles herein can be configured to train a predictive model of a measure of the cognitive capabilities of individuals based on the data measured from the performance at the navigation tasks (allocentric and/or egocentric navigation tasks) of individuals that are previously classified as to the measure of cognitive abilities of interest. For example, a classifier can be trained using a plurality of training datasets, where each training dataset is associated with a previously classified individual from a group of individuals. Each of the training dataset includes data indicative of one or more parameters indicative of the performance of the classified individual at the task(s) (whether allocentric and/or egocentric navigation tasks), based on the classified individual's interaction with an example apparatus, system, or computing device described herein. The example classifier also can take as input data indicative of the performance of the classified individual at a cognitive test, and/or a behavioral test, and/or data indicative of a diagnosis of a likelihood of onset of, or stage of progression of, a neurodegenerative cognitive condition, a disease, or a disorder (including an executive function disorder) of the classified individual.

In any example herein, the example trained predictive model can be used as an intelligent proxy for quantifiable assessments of an individual's cognitive abilities. That is, once a predictive model is trained, the predictive model output can be used to provide the indication of the cognitive capabilities of multiple individuals without use of a physiological measure, or another cognitive or behavioral assessment tests. In an example, the trained predictive model can be used as an intelligent proxy to provide an indication of a likelihood of onset of a neurodegenerative condition of the individual, or the stage of progression of the neurodegenerative condition. In an example, the trained predictive model can be used as an intelligent proxy for subsequent measures of the neurodegenerative condition of the individual.

An example system, method, and apparatus according to the principles herein includes a platform product (including using an APP) that is configured to present any combination of one or more of the above-described performance metrics with standard cognitive tasks for navigation, such as the pathway span task, the dynamic maze task, the radial arm maze, the morris water navigation task. Through correlation of the results of the multiple performance measures described herein and two or more of the standard cognitive tasks, the combinations allow for greater precision in assessing brain function of an individual or group of individuals, standards setting, calibration of one metric as compared to another metric, and validation or corroboration of the results of one or the tools versus the others. That is, the standard cognitive tasks may test one type of navigation capability of the individual. However, the systems, methods, and apparatus herein provides for methods, and apparatus described herein can be used to generate indicators of the relative capabilities of the allocentric tasks versus the egocentric tasks.

An example system, method, and apparatus according to the principles herein includes a platform product (including using an APP) that is configured to present any combination of one or more of the above-described performance metrics with an interference processing or other multi-tasking task (such as but not limited to the dual task measurements performed using the Project: EVO™ platform.

An example system, method, and apparatus according to the principles herein includes a platform product (including using an APP) that is configured to present any combination of one or more of the above-described performance metrics with measurements of gross and fine motor function (as nData).

An example system, method, and apparatus according to the principles herein includes a platform product (including using an APP) that is configured to present any combination of one or more of the above-described performance metrics with standard cognitive tasks for working memory, such as spatial working memory. Through correlation of the results of the multiple performance measures described herein and two or more of the standard cognitive tasks, the combinations allow for greater precision in assessing brain function of an individual or group of individuals, standards setting, calibration of one metric as compared to another metric, and validation or corroboration of the results of one or the tools versus the others.

An example system, method, and apparatus according to the principles herein includes a platform product (including using an APP) that is configured to present any combination of one or more of the above-described performance metrics with voice/speech monitoring based measures of cognitive and behavioral health. Through correlation of the results of the multiple performance measures described herein and two or more of the standard cognitive tasks, the combinations allow for greater precision in assessing brain function of an individual or group of individuals, standards setting, calibration of one metric as compared to another metric, and validation or corroboration of the results of one or the tools versus the others.

An example system, method, and apparatus according to the principles herein includes a platform product (including using an APP) that is configured to improve allocentric navigation as a treatment. For example, the example platform product can be configured to adapt and/or increase the difficulty level of the navigation task(as) to improve wayfinding function. For example, the platform product can be configured to make it harder for the individual to rely on allocentric navigation by reducing the number of landmarks presented to the individual fur use in a virtual space over time. As another example, the platform product can be configured to expand the size of the virtual environment so that there is more information for an individual to evaluate in order to make choices in the navigation. As another example, the platform product can be configured to make multiple virtual environments with the same visual landmarks in different positions so that interference of the landmark reduces the use of egocentric navigation. As another example, the platform product can be configured to present maps to the individual with increasingly incomplete information (for example, by gradually reducing the number of landmarks present in the landscape). As another example, the platform product can be configured to put obstacles in the way of the known/previously trained route to increase difficulty and force an individual to use allocentric navigation techniques. As another example, the platform product can be configured to place starting points and one or more targets in different locations than in a previous session in a given environment, to force an individual to use allocentric strategies. As another example, the platform product can be configured to cause the individual to interact with environments analogous to previously explored environments and require the individual to employ knowledge of the source environment to reach the one or more targets in the second environment, where the degree of difference between the source and analogous (second) environments may vary as desired. As another example, the platform product can be configured to introduce interfering activities of varying difficulty and/or duration in between navigation trials to stress maintenance and retrieval of spatial memory. As another example, the platform product can be configured to vary the number of possible source environments for an analogous (second) environment and/or the amount of information or time available with which to determine which is the source environment. As another example, the platform product can be configured to present any combination of two or more of these changes at substantially the same time or at differing times within the same session.

An example system, method, and apparatus according to the principles herein includes a platform product (including using an APP) that is configured to communicate with a physiological measurement component for measuring nData (from physiological measurements). For example, to determine whether a person is actually using allocentric navigation or egocentric navigation can be confirmed via fMRI while the individual performing a navigation task. If fMRI indicates that there is activity in the hippocampus (i.e. nData showing stronger bold fMRI contrast in this region of the brain), the individual is likely using an allocentric strategy. If fMRI indicates that there is activity in the caudate nucleus (i.e. nData showing stronger bold fMRI contrast in this region of the brain), the person is likely using an egocentric strategy.

The strength of hippocampal function can correlate with structural MRI measurements such as volume, cortical thickness, etc. This in turn can correlate with the ability of an individual to use allocentric navigation. The strength of caudate nucleus function can correlate with volume, and the ability of an individual to use egocentric navigation.

Changes in hippocampal volume, e.g. decreases resulting from disease progression or increases as a result of therapy, can correlate with an increase in the individual's ability to use allocentric navigation. Measurements of allocentric strategy efficiency can be used as indicators of disease progress or treatment efficacy. Such measures also can be used to determine the appropriate levels of difficulty to be used in the navigation-based treatment using the platform product(s) described herein.

As a non-limiting example, the cognitive platform based on interference processing can be the Project: EVO™ platform by Akili Interactive Labs, Inc., Boston, MA.

An example system, method, and apparatus according to the principles herein includes a platform product (including using an APP) that is configured to set baseline performance metrics at the navigation task(s) in APP session(s) based on measurements nData indicative of physiological condition and/or cognition condition (including indicators of neuropsychological disorders), to increase accuracy of assessment and efficiency of treatment. The CSIs may be used to calibrate a nData component to individual user dynamics of nData.

An example system, method, and apparatus according to the principles herein includes a platform product (including using an APP) that is configured to use nData to detect states of attentiveness or inattentiveness to optimize delivery of navigation task(s) related to treatment or assessment.

An example system, method, and apparatus according to the principles herein includes a platform product (including using an APP) that is configured to use analysis of nData with navigation task(s) cData to detect and direct attention to specific CSIs related to treatment or assessment through subtle or overt manipulation of CSIs.

An example system, method, and apparatus according to the principles herein includes a platform product (including using an APP) that is configured to monitor nData indicative of anger and/or frustration to promote continued user interaction with the cognitive platform by offering alternative navigation task(s) or disengagement from the navigation task(s).

An example system, method, and apparatus according to the principles herein includes a platform product (including using an APP) that is configured to combine signals from navigation task(s) cData with nData to optimize individualized treatment promoting improvement of indicators of cognitive abilities, and thereby, cognition.

An example system, method, and apparatus according to the principles herein includes a platform product (including using an APP) that is configured to use a profile of nData to confirm/verify/authenticate a user's identity.

An example system, method, and apparatus according to the principles herein includes a platform product (including using an APP) that is configured to use nData to detect positive emotional response to CSIs in navigation task(s) in order to catalog individual user preferences to customize CSIs to optimize enjoyment and promote continued engagement with assessment or treatment sessions.

An example system, method, and apparatus according to the principles herein includes a platform product (including using an APP) that is configured to generate user profiles of cognitive improvement (such as but not limited to, user profiles associated with users classified or known to exhibit improved working memory, attention, processing speed, and/or perceptual detection/discrimination), and deliver a treatment that adapts navigation task(s) to optimize the profile of a new user as confirmed by profiles from nData.

An example system, method, and apparatus according to the principles herein includes a platform product (including using an APP) that is configured to provide to a user a selection of one or more profiles configured for cognitive improvement.

An example system, method, and apparatus according to the principles herein includes a platform product (including using an APP) that is configured to monitor nData from auditory and visual physiological measurements to detect interference from external environmental sources that may interfere with the assessment or treatment being performed by a user using an APP.

An example system, method, and apparatus according to the principles herein includes a platform product (including using an APP) that is configured to use cData and/or nData (including metrics from analyzing the data) as a determinant or to make a decision as to whether a user (including a patient using a medical device) is likely to respond or not to respond to a treatment (such as but not limited to a cognitive treatment and/or a treatment using a biologic, a drug or other pharmaceutical agent). For example, the system, method, and apparatus can be configured to select whether a user (including a patient using a medical device) should receive treatment based on specific physiological or cognitive measurements that can be used as signatures that have been validated to predict efficacy in a given individual or certain individuals of the population (e.g., individual(s) classified to a given group based on amyloid status). Such an example system, method, and apparatus configured to perform the analysis (and associated computation) described herein can be used as a biomarker to perform monitoring and/or screening. As a non-limiting example, the example system, method and apparatus configured to provide a provide a quantitative measure of the degree of efficacy of a cognitive treatment (including the degree of efficacy in conjunction with use of a biologic, a drug or other pharmaceutical agent) for a given individual or certain individuals of the population (e.g., individual(s) classified to a given group based on amyloid status). In some examples, the individual or certain individuals of the population may be classified as having a certain condition, including a neurodegenerative condition.

An example system, method, and apparatus according to the principles herein includes a platform product (including using an APP) that is configured to use nData to monitor a user's ability to anticipate the course of navigation task(s) and manipulate navigation task(s) patterns and/or rules to disrupt user anticipation of response to navigation task(s), to optimize treatment or assessment in an APP.

Figure 2:
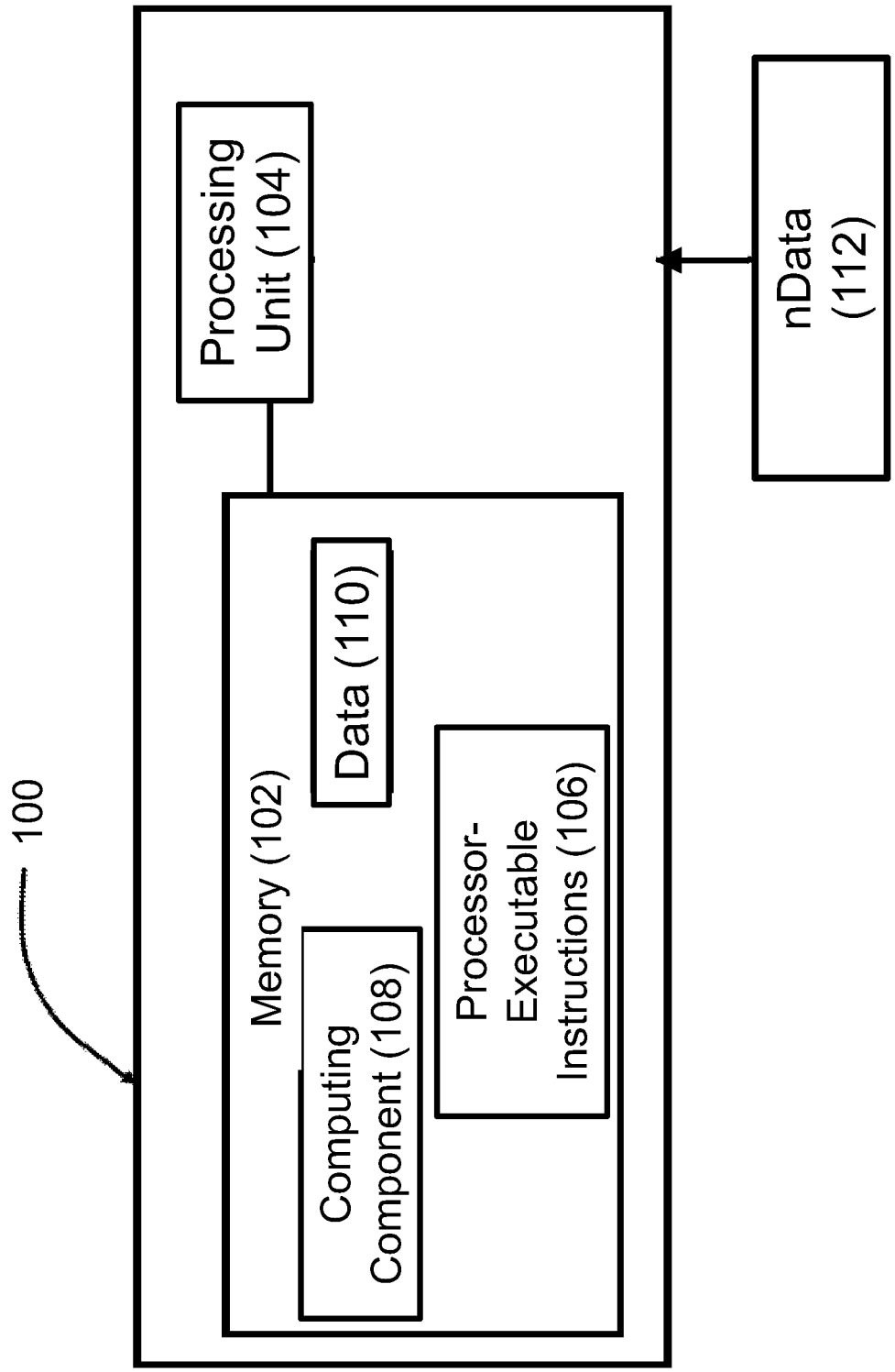
FIG. 2 shows an example apparatus, according to the principles herein.

Non-limiting examples of analysis (and associated computations) that can be performed based on various combinations of different types of nData and cData are described. The following example analyses and associated computations can be implemented using any example system, method and apparatus according to the principles herein. As described hereinabove, the example systems, methods, and apparatus according to the principles herein can be implemented, using at least one processing unit of a programmed computing device, to provide the cognitive platform of a platform product. FIG. 2 shows an example apparatus 100 according to the principles herein that can be used to implement the cognitive platform described hereinabove herein. The example apparatus 100 includes at least one memory 102 and at least one processing unit 104. The at least one processing unit 104 is communicatively coupled to the at least one memory 102.

Example memory 102 can include, but is not limited to, hardware memory, non-transitory tangible media, magnetic storage disks, optical disks, flash drives, computational device memory, random access memory, such as but not limited to DRAM, SRAM, EDO RAM, any other type of memory, or combinations thereof. Example processing unit 104 can include, but is not limited to, a microchip, a processor, a microprocessor, a special purpose processor, an application specific integrated circuit, a microcontroller, a field programmable gate array, any other suitable processor, or combinations thereof.

The at least one memory 102 is configured to store processor-executable instructions 106 and a computing component 108. In a non-limiting example, the computing component 108 can be used to analyze the cData and/or nData received from the cognitive platform coupled with the one or more physiological or monitoring components and/or cognitive testing components as described herein. As shown in FIG. 2, the memory 102 also can be used to store data 110, such as but not limited to the nData 112 (including measurement data from measurement(s) using one or more physiological or monitoring components and/or cognitive testing components) and/or data indicative of the response of an individual to the one or more tasks (cData), including responses to tasks rendered at a graphical user interface of the apparatus 100 and/or tasks generated using an auditory, tactile, or vibrational signal from an actuating component coupled to or integral with the apparatus 100. The data 110 can be received from one or more physiological or monitoring components and/or cognitive testing components that are coupled to or integral with the apparatus 100.

In a non-limiting example, the at least one processing unit 104 executes the processor-executable instructions 106 stored in the memory 102 at least to analyze the cData and/or nData received from the cognitive platform coupled with the one or more physiological or monitoring components and/or cognitive testing components as described herein, using the computing component 108. The at least one processing unit 104 also executes processor-executable instructions 106 to control a transmission unit to transmit values indicative of the analysis of the cData and/or nData received from the cognitive platform coupled with the one or more physiological or monitoring components and/or cognitive testing components as described herein, and/or controls the memory 102 to store values indicative of the analysis of the cData and/or nData.

In another non-limiting example, the at least one processing unit 104 executes the processor-executable instructions 106 stored in the memory 102 at least to apply signal detection metrics in computer-implemented adaptive response-deadline procedures.

Figure 3:
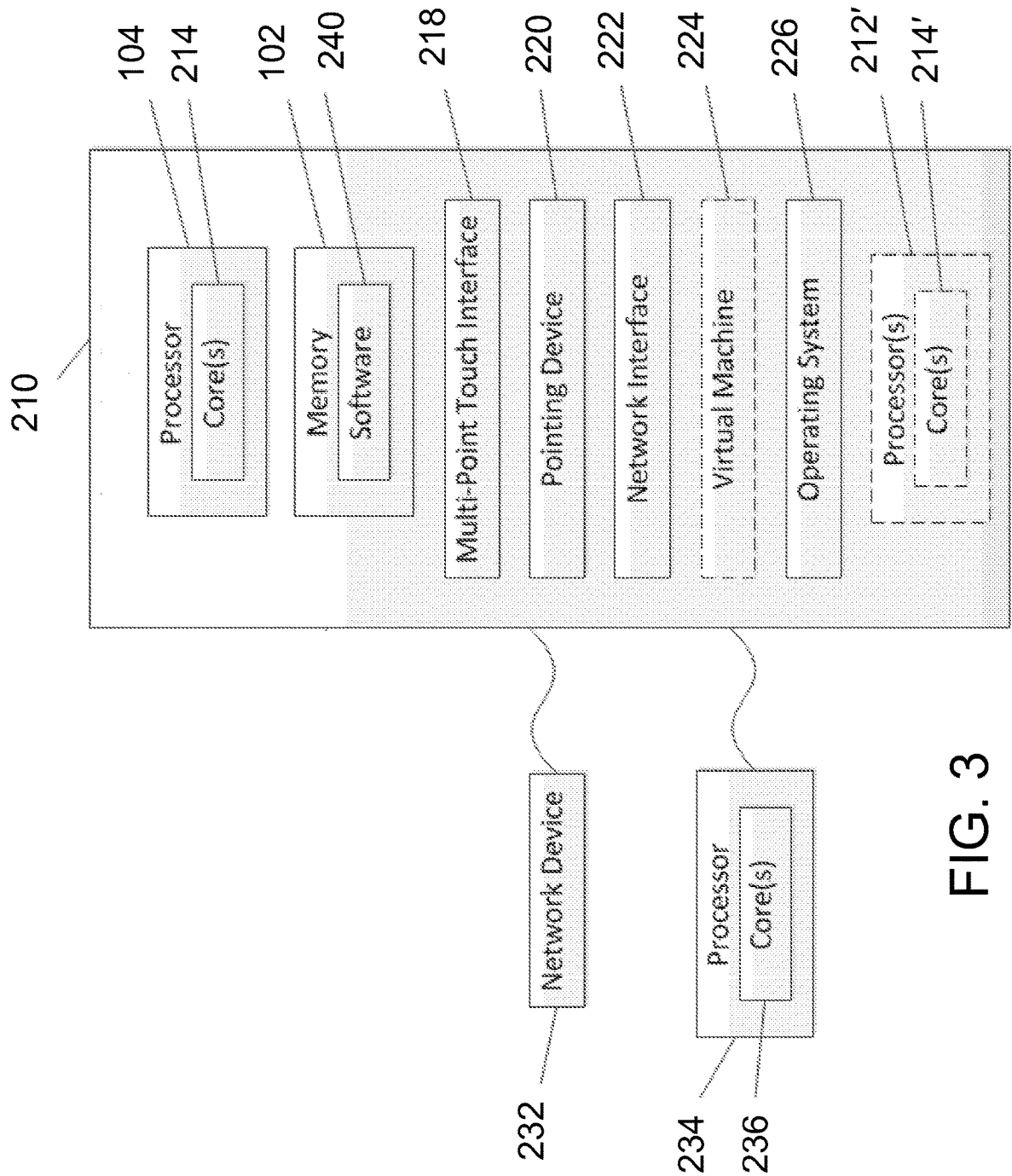
FIG. 3 shows a block diagram of an example computing device, according to the principles herein.

FIG. 3 is a block diagram of an example computing device 210 that can be used as a computing component according to the principles herein. In any example herein, computing device 210 can be configured as a console that receives user input to implement the computing component, including to apply the signal detection metrics in computer-implemented adaptive response-deadline procedures. For clarity, FIG. 3 also refers back to and provides greater detail regarding various elements of the example system of FIG. 2. The computing device 210 can include one or more non-transitory computer-readable media for storing one or more computer-executable instructions or software for implementing examples. The non-transitory computer-readable media can include, but are not limited to, one or more types of hardware memory, non-transitory tangible media (for example, one or more magnetic storage disks, one or more optical disks, one or more flash drives), and the like. For example, memory 102 included in the computing device 210 can store computer-readable and computer-executable instructions or software for performing the operations disclosed herein. For example, the memory 102 can store a software application 240 which is configured to perform various of the disclosed operations (e.g., analyze cognitive platform measurement data and response data, apply a signal detection metrics in adaptive response-deadline procedures, or performing a computation). The computing device 210 also includes configurable and/or programmable processor 104 and an associated core 214, and optionally, one or more additional configurable and/or programmable processing devices, e.g., processor(s) 212' and associated core(s) 214' (for example, in the case of computational devices having multiple processors/cores), for executing computer-readable and computer-executable instructions or software stored in the memory 102 and other programs for controlling system hardware. Processor 104 and processor(s) 212' can each be a single core processor or multiple core (214 and 214') processor.

Virtualization can be employed in the computing device 210 so that infrastructure and resources in the console can be shared dynamically. A virtual machine 224 can be provided to handle a process running on multiple processors so that the process appears to be using only one computing resource rather than multiple computing resources. Multiple virtual machines can also be used with one processor.

Memory 102 can include a computational device memory or random access memory, such as but not limited to DRAM, SRAM, EDO RAM, and the like. Memory 102 can include a non-volatile memory, such as but not limited to a hard-disk or flash memory. Memory 102 can include other types of memory as well, or combinations thereof.

In a non-limiting example, the memory 102 and at least one processing unit 104 can be components of a peripheral device, such as but not limited to a dongle (including an adapter) or other peripheral hardware. The example peripheral device can be programmed communicate with or otherwise couple to a primary computing device, to provide the functionality of any of the example cognitive platform and/or platform product, and implement any of the example analyses (including the associated computations) described herein. In some examples, the peripheral device can be programmed to directly communicate with or otherwise couple to the primary computing device (such as but not limited to via a USB or HDMI input), or indirectly via a cable (including a coaxial cable), copper wire (including, but not limited to, PSTN, ISDN, and DSL), optical fiber, or other connector or adapter. In another example, the peripheral device can be programmed to communicate wirelessly (such as but not limited to Wi-Fi or Bluetooth®) with primary computing device. The example primary computing device can be a smartphone (such as but not limited to an iPhone®, a BlackBerry®, or an Android™-based smartphone), a television, a workstation, a desktop computer, a laptop, a tablet, a slate, an electronic-reader (e-reader), a digital assistant, or other electronic reader or hand-held, portable, or wearable computing device, or any other equivalent device, a gaming device (such as but not limited to an Xbox®, or a Wii®), or other equivalent form of computing device.

A user can interact with the computing device 210 through a visual display unit 228, such as a computer monitor, which can display one or more user interfaces 230 that can be provided in accordance with example systems and methods. The computing device 210 can include other I/O devices for receiving input from a user, for example, a keyboard or any suitable multi-point touch interface 218, a pointing device 220 (e.g., a mouse), a camera or other image recording device, a microphone or other sound recording device, an accelerometer, a gyroscope, a sensor for tactile, vibrational, or auditory signal, and/or at least one actuator. The keyboard 218 and the pointing device 220 can be coupled to the visual display unit 228. The computing device 210 can include other suitable conventional I/O peripherals.

The computing device 210 can also include one or more storage devices 234, such as a hard-drive, CD-ROM, or other computer readable media, for storing data and computer-readable instructions and/or software that perform operations disclosed herein. Example storage device 234 can also store one or more databases for storing any suitable information required to implement example systems and methods. The databases can be updated manually or automatically at any suitable time to add, delete, and/or update one or more items in the databases.

The computing device 210 can include a network interface 222 configured to interface via one or more network devices 232 with one or more networks, for example, Local Area Network (LAN), metropolitan area network (MAN), Wide Area Network (WAN) or the Internet through a variety of connections including, but not limited to, standard telephone lines, LAN or WAN links (for example, 802.11, T1, T3, 56kb, X.25), broadband connections (for example, ISDN, Frame Relay, ATM), wireless connections, controller area network (CAN), or some combination of any or all of the above. The network interface 222 can include a built-in network adapter, network interface card, PCMCIA network card, card bus network adapter, wireless network adapter, USB network adapter, modem or any other device suitable for interfacing the computing device 210 to any type of network capable of communication and performing the operations described herein. Moreover, the computing device 210 can be any computational device, such as a smartphone (such as but not limited to an iPhone®, a BlackBerry®, or an Android™-based smartphone), a television, a workstation, a desktop computer, a server, a laptop, a tablet, a slate, an electronic-reader (e-reader), a digital assistant, or other electronic reader or hand-held, portable, or wearable computing device, or any other equivalent device, an Xbox®, a Wii®, or other equivalent form of computing or telecommunications device that is capable of communication and that has or can be coupled to sufficient processor power and memory capacity to perform the operations described herein. The one or more network devices 232 may communicate using different types of protocols, such as but not limited to WAP (Wireless Application Protocol), TCP/IP (Transmission Control Protocol/Internet Protocol), NetBEUI (NetBIOS Extended User Interface), or IPX/SPX (Internetwork Packet Exchange/Sequenced Packet Exchange).

The computing device 210 can run any operating system 226, such as any of the versions of the Microsoft® Windows® operating systems, iOS® operating system, Android™ operating system, the different releases of the Unix and Linux operating systems, any version of the MacOS® for Macintosh computers, any embedded operating system, any real-time operating system, any open source operating system, any proprietary operating system, or any other operating system capable of running on the console and performing the operations described herein. In some examples, the operating system 226 can be run in native mode or emulated mode. In an example, the operating system 226 can be run on one or more cloud machine instances.

Figure 4A:
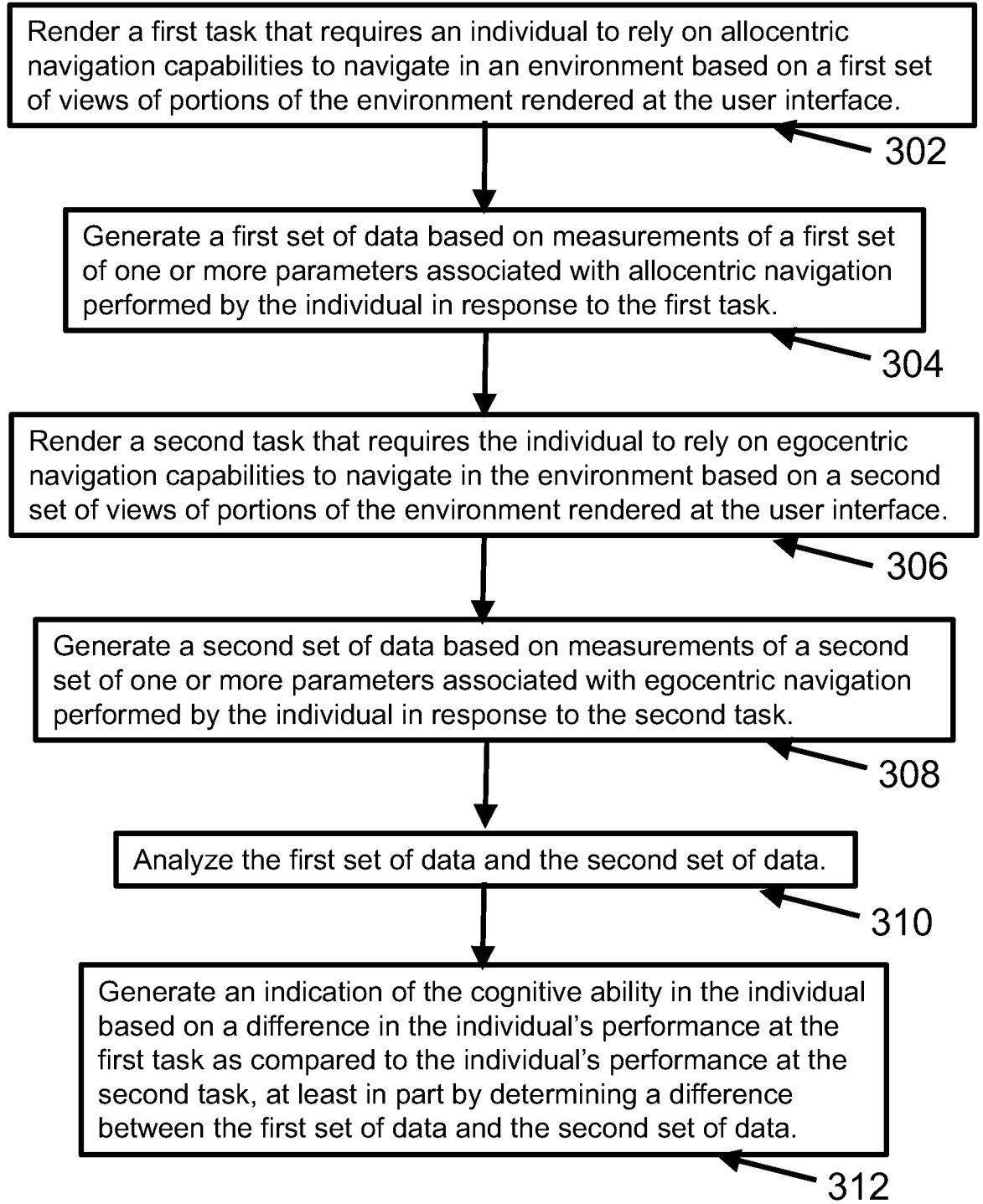

FIG. 4A shows a flowchart of a non-limiting example method that can be implemented using a cognitive platform or platform product that includes at least one processing unit. The example cognitive platform or platform product includes a memory to store processor-executable instructions, and one or more processing units communicatively coupled to the user interface and the memory. Upon execution of the processor-executable instructions by the one or more processing units, the one or more processing units are configured to execute the method in the flowchart of FIG. 4A. In block 302, the one or more processing units are used to render a first task that requires an individual to rely on allocentric navigation capabilities to navigate in an environment based on a first set of views of portions of the environment rendered at the user interface. In block 304, the one or more processing units are used to generate a first set of data based on measurements of a first set of one or more parameters associated with allocentric navigation performed by the individual in response to the first task. In block 306, the one or more processing units are used to render a second task that requires the individual to rely on egocentric navigation capabilities to navigate in the environment based on a second set of views of portions of the environment rendered at the user interface. In block 308, the one or more processing units are used to generate a second set of data based on measurements of a second set of one or more parameters associated with egocentric navigation performed by the individual in response to the second task. In block 310, the one or more processing units are used to analyze the first set of data and the second set of data. In block 312, the one or more processing units are used to generate an indication of the cognitive ability in the individual based on a difference in the individual's performance at the first task as compared to the individual's performance at the second task, at least in part by determining a difference between the first set of data and the second set of data.

Figure 4B:
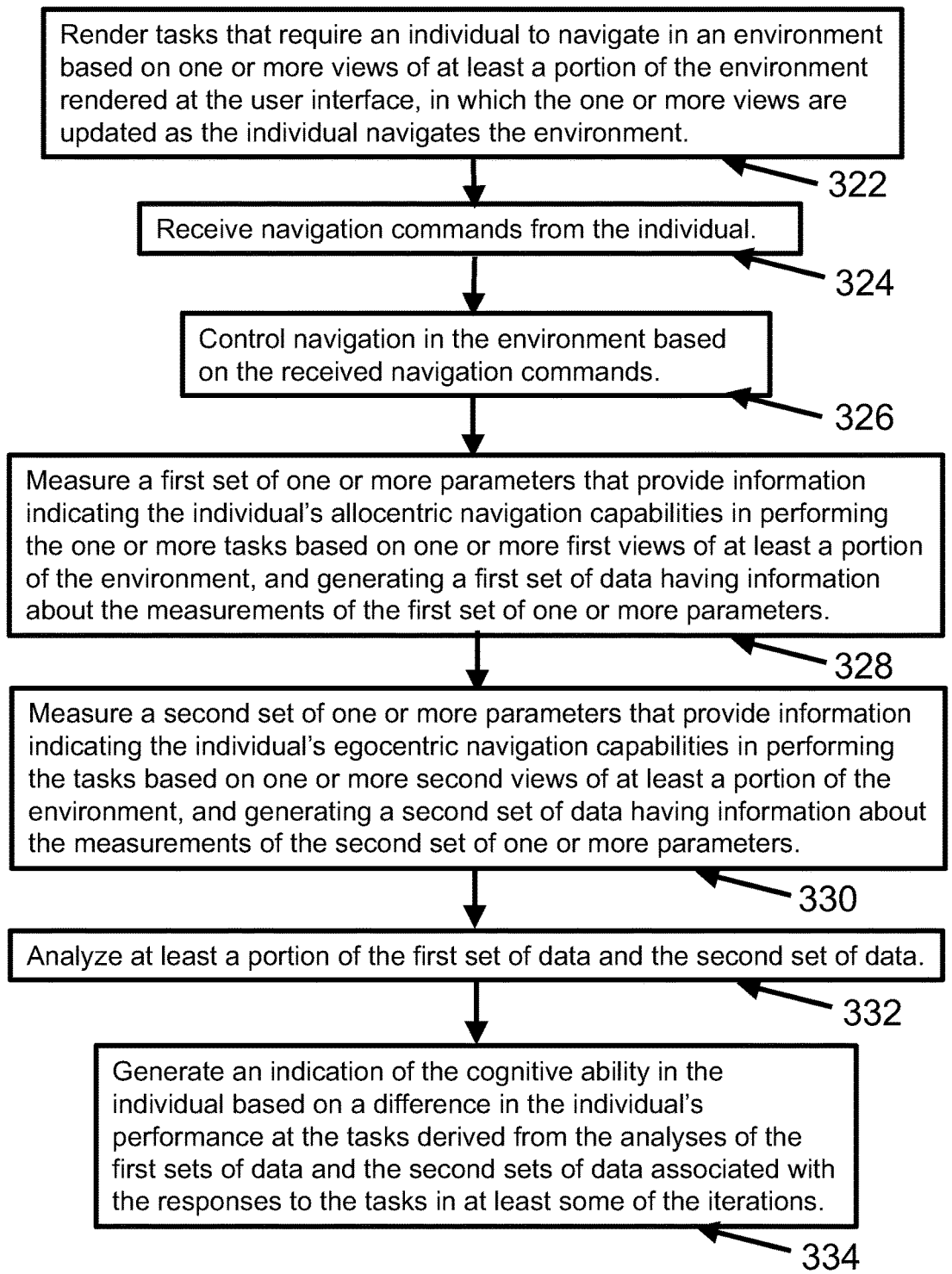

FIG. 4B shows a flowchart of a non-limiting example method that can be implemented using a cognitive platform or platform product that includes at least one processing unit. The example cognitive platform or platform product includes a memory to store processor-executable instructions, and one or more processing units communicatively coupled to the user interface and the memory. Upon execution of the processor-executable instructions by the one or more processing units, the one or more processing units are configured to execute the method in the flowchart of FIG. 4B. The one or more processing units are configured to iteratively perform, in a series of at least two iterations, the procedures in blocks 322 through 334. In block 322, the one or more processing units are used to render tasks that require an individual to navigate in an environment based on one or more views of at least a portion of the environment rendered at the user interface, in which the one or more views are updated as the individual navigates the environment. In block 324, the one or more processing units are used to receive navigation commands from the individual. In block 326, the one or more processing units are used to control navigation in the environment based on the received navigation commands. In block 328, the one or more processing units are used to measure a first set of one or more parameters that provide information indicating the individual's allocentric navigation capabilities in performing the one or more tasks based on one or more first views of at least a portion of the environment, and generating a first set of data having information about the measurements of the first set of one or more parameters. In block 330, the one or more processing units are used to measure a second set of one or more parameters that provide information indicating the individual's egocentric navigation capabilities in performing the tasks based on one or more second views of at least a portion of the environment, and generating a second set of data having information about the measurements of the second set of one or more parameters. In block 332, the one or more processing units are used to analyze at least a portion of the first set of data and the second set of data. The task rendered in a second iteration or a later iteration is determined based at least in part on the analysis of at least one of the first set of data and the second set of data associated with one or more parameters measured in one or more previous iterations. In block 334, the one or more processing units are used to generate an indication of the cognitive ability in the individual based on a difference in the individual's performance at the tasks derived from the analyses of the first sets of data and the second sets of data associated with the responses to the tasks in at least some of the iterations.

Figure 4C:
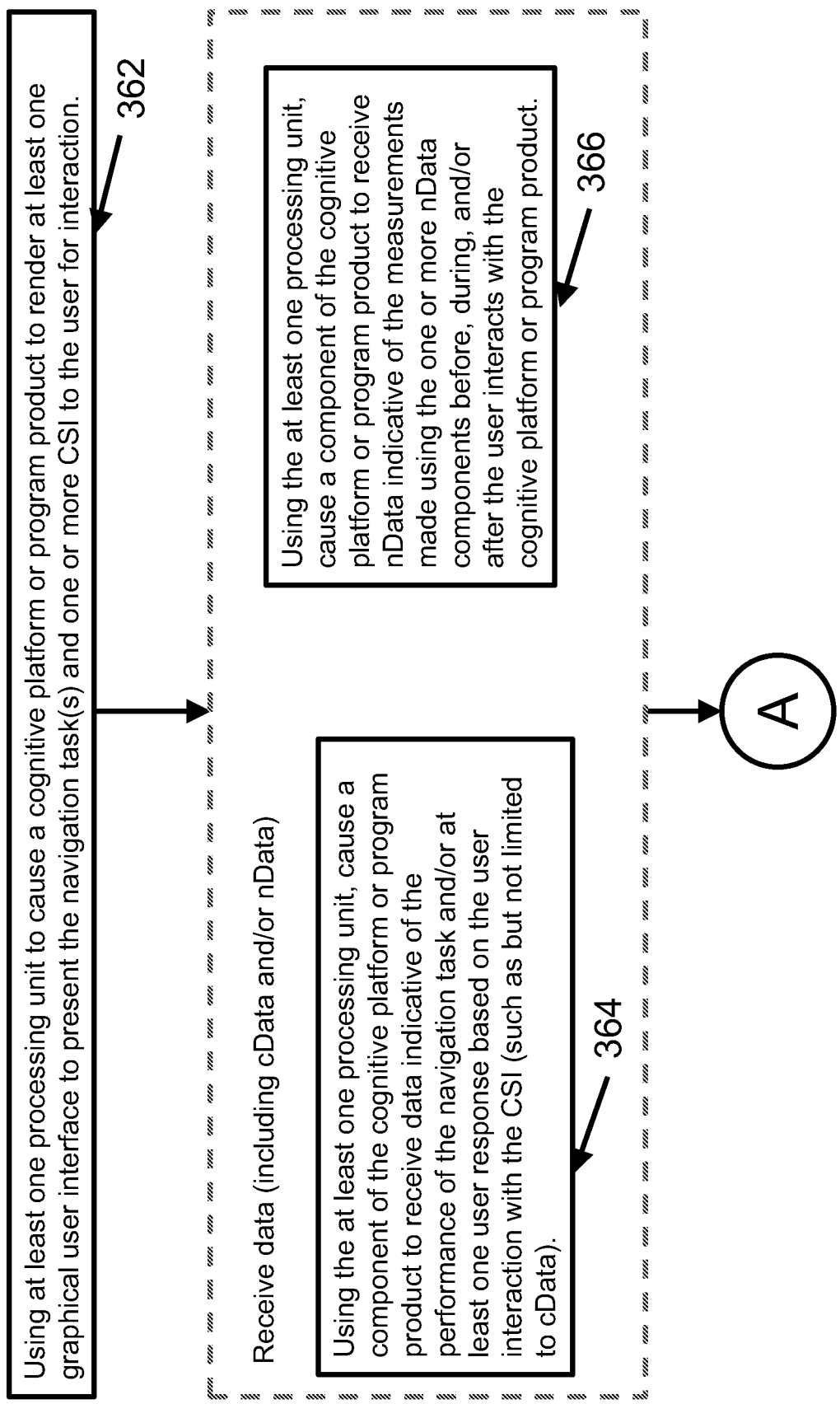

FIGS. 4C-4D show a flowchart of a non-limiting example method that can be implemented using a cognitive platform or platform product that includes at least one processing unit. In block 362, the at least one processing unit Is used to render at least one graphical user interface to present the navigation task(s) and one or more CSI to the user for interaction. In block 364, the at least one processing unit is used to cause a cause a component of the program product to receive data indicative of the performance of the navigation task and/or at least one user response based on the user interaction with the CSI (such as but not limited to cData), including responses provided using the input device. In block 366, the at least one processing unit is used to cause a component of the program product to receive nData indicative of measurements made before, during, and/or after the user interacts with the cognitive platform (including nData from measurements of physiological or monitoring components and/or cognitive testing components). In an example implementation of the method, block 364 may be performed in a similar timeframe, or substantially simultaneously with block 366. In another example implementation of the method, block 364 may be performed at different timepoints than block 366. In block 368, the at least one processing unit also is used to: analyze the cData and/or nData to provide a measure of the individual's condition (including cognitive condition), and/or analyze the cData and/or nData to provide a measure of the individual's performance metric for a given type of navigation task (whether the navigation task requires allocentric navigation and/or egocentric navigation), and/or analyze the differences in the individual's performance based on determining the differences between the user's performance at allocentric navigation as compared to the user's performance at egocentric navigation (including based on differences in the cData) and differences in the associated nData, and/or adjust the difficulty level of the navigation task(s) (including CSIs), based on the analysis of the cData (including the measures of the individual's performance determined in the analysis), and/or provide an output or other feedback from the platform product that can be indicative of the individual's performance metric, and/or cognitive abilities (including for screening, monitoring or assessment), and/or response to cognitive treatment, and/or assessed measures of cognition, and/or classify an individual as to amyloid status, and/or presence or expression level of tau proteins, and/or potential efficacy of use of the cognitive platform or platform product when the individual is administered a drug, biologic or other pharmaceutical agent, and/or expected score from the individual's performance of a TOVA® test and/or a RAVLT™ test, and/or classify an individual as to likelihood of onset and/or stage of progression of a condition, and/or to determine a change in dosage (amount, concentration, or dose titration) of a drug, biologic or other pharmaceutical agent to the individual or to determine an optimal type or combination of drug, biologic or other pharmaceutical agent to the individual, based on nData and the cData collected from the individual's interaction with the cognitive platform or platform product and/or metrics computed based on the analysis (and associated computations) of that cData and the nData.

In an example system, method and apparatus, prior to rendering the tasks at the user interface, the at least one processing unit is configured to cause a component of the program product to receive nData indicative of one or more of an amount, concentration, or dose titration of a pharmaceutical agent, drug, or biologic being or to be administered to an individual. Based at least in part on the analysis of the cData collected from the individual's performance of the navigation task(s), the at least one processing unit is configured to generate an output to the user interface indicative of a change in the individual's cognitive ability.

Any classification of an individual as to likelihood of onset and/or stage of progression of a condition (including a neurodegenerative condition) in block 368 can be transmitted as a signal to a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in dosage (amount, concentration, or dose titration) of a drug, biologic or other pharmaceutical agent to the individual or to determine an optimal type or combination of drug, biologic or other pharmaceutical agent to the individual.

In some examples, the results of the analysis may be used to modify the difficulty level or other property of the navigation task(s) or CSIs.

Figure 5A:
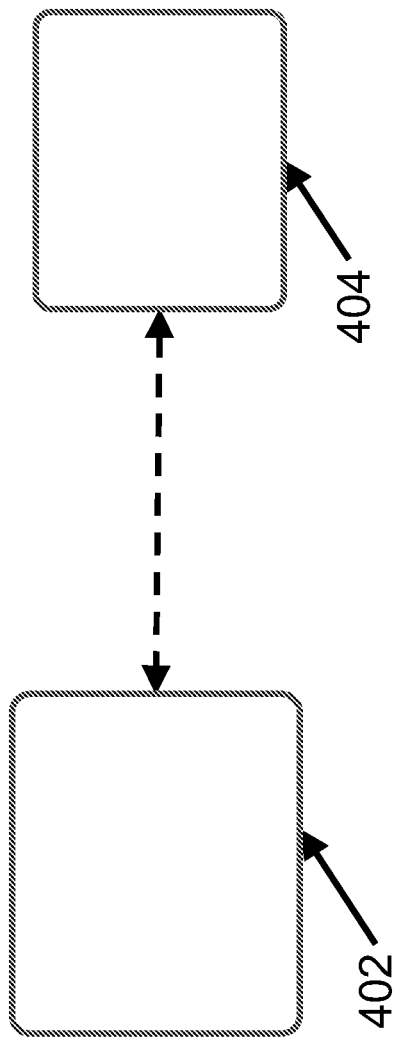
FIG. 5A shows an example system including a cognitive platform coupled with physiological component(s), according to the principles herein.

FIG. 5A shows a non-limiting example system, method, and apparatus according to the principles herein, where the platform product (including using an APP) is configured as a cognitive platform 402 that is separate from, but configured for coupling with, one or more of the physiological components 404.

Figure 5B:
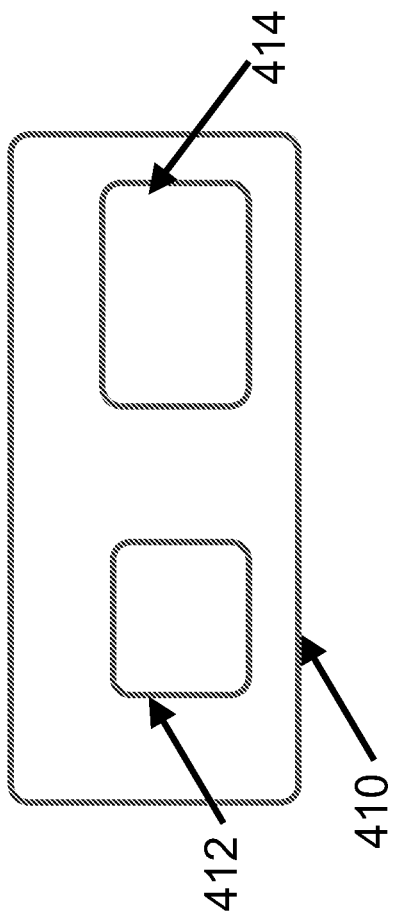
FIG. 5B shows an example system configured as a cognitive platform integrated with physiological component(s), according to the principles herein.

FIG. 5B shows another non-limiting example system, method, and apparatus according to the principles herein, where the platform product (including using an APP) is configured as an integrated device 410, where the cognitive platform 412 that is integrated with one or more of the physiological components 414.

Figure 6:
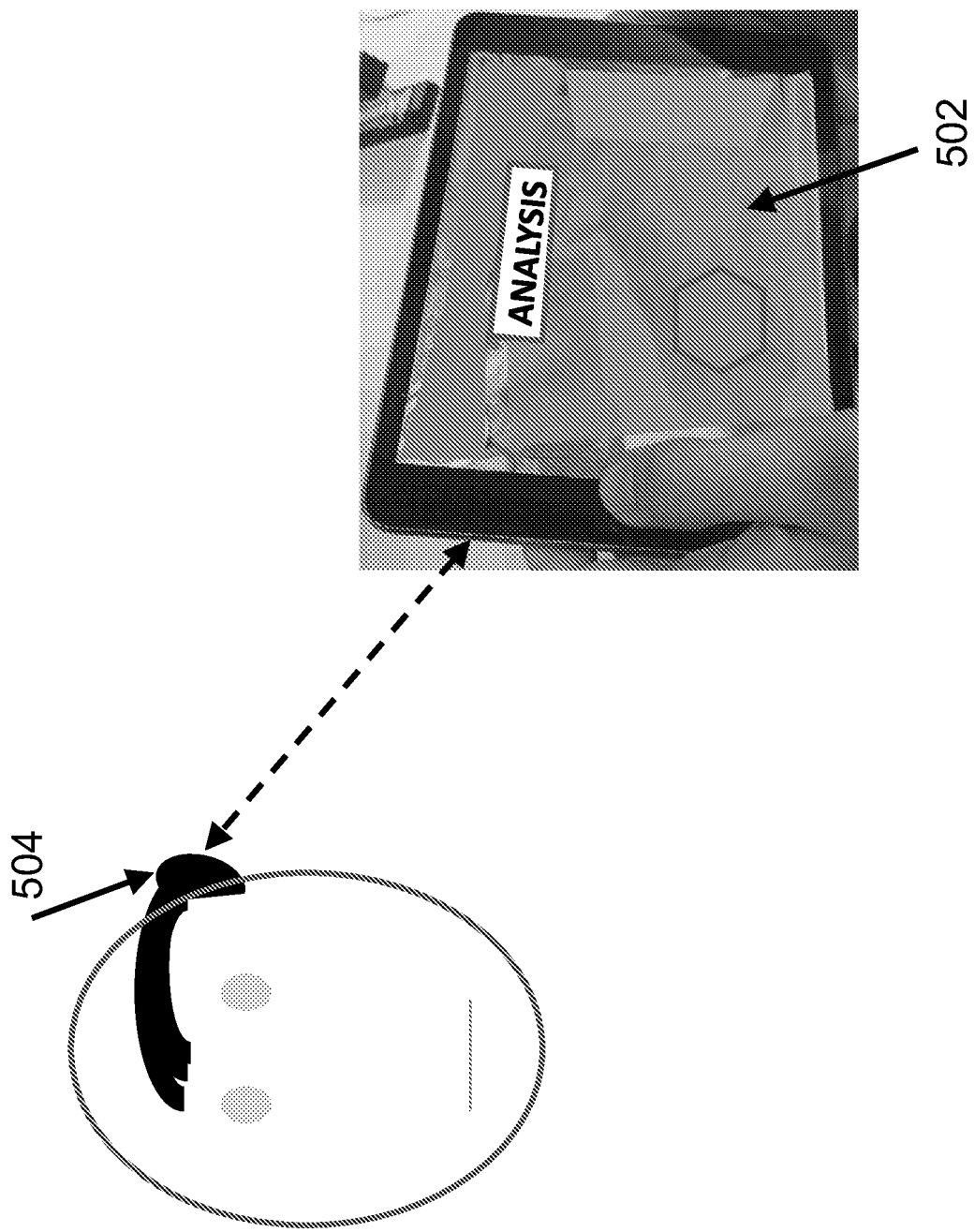
FIG. 6 shows an example system including a cognitive platform coupled with physiological component(s), according to the principles herein.

FIG. 6 shows a non-limiting example implementation where the platform product (including using an APP) is configured as a cognitive platform 502 that is configured for coupling with a physiological component 504. In this example, the cognitive platform 502 is configured as a tablet including at least one processor programmed to implement the processor-executable instructions associated with the tasks and CSIs described hereinabove, to receive cData associated with user responses from the user interaction with the cognitive platform 502, to receive the nData from the physiological component 504, to analyze the cData and/or nData as described hereinabove, and to analyze the cData and/or nData to provide a measure of the individual's physiological condition and/or cognitive condition, and/or analyze the differences in the individual's performance based on determining the differences between the user's responses and the nData, and/or adjust the difficulty level of the computerized stimuli or interaction (CSI) or other interactive elements based on the individual's performance determined in the analysis and based on the analysis of the cData and/or nData, and/or provide an output or other feedback from the platform product indicative of the individual's performance, and/or cognitive assessment, and/or response to cognitive treatment, and/or assessed measures of cognition. In this example, the physiological component 504 is mounted to a user's head, to perform the measurements before, during and/or after user interaction with the cognitive platform 502, to provide the nData.

In a non-limiting example implementation, measurements are made using a cognitive platform that is configured for coupling with a fMRI, for use for medical application validation and personalized medicine. Consumer-level fMRI devices may be used to improve the accuracy and the validity of medical applications by tracking and detecting changes in brain part stimulation.

In a non-limiting example, fMRI measurements can be used to provide measurement data of the cortical thickness and other similar measurement data.

In a non-limiting example use for treatment validation, the user interacts with a cognitive platform, and the fMRI is used to measure physiological data. The user is expected to have stimulation of a particular brain part or combination of brain parts based on the actions of the user while interacting with the cognitive platform. In this example, the platform product may be configured as an integrated device including the fMRI component coupled with the cognitive platform, or as a cognitive platform that is separate from, but configured for coupling with the fMRI component. Using the application with the fMRI, measurement can be made of the stimulation of portions of the user brain, and analysis can be performed to detect changes to determining whether the user is exhibit the desired responses.

In a non-limiting example use for personalized medicine, the fMRI can be used to collect measurement data to be used to identify the progress of the user in interacting with the cognitive platform. The analysis can be used to determine whether the cognitive platform should be caused to provide tasks and/or CSIs to enforce or diminish these user results that the fMRI is detecting, by adjusting users experience in the application.

In any example herein, the adjustments to the type of navigation tasks and/or CSIs can be made in real-time.

Conclusion

The above-described embodiments can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An apparatus for generating an assessment of one or more cognitive skills in an individual, said apparatus comprising:
   a user interface comprising a display and at least one input device;
   a memory to store processor-executable instructions; and
   one or more processing units communicatively coupled to the user interface and the memory, wherein upon execution of the processor-executable instructions by the one or more processing units, the one or more processing units are configured to:
   render a first task at the user interface, wherein the first task requires an individual to rely on allocentric navigation capabilities to navigate in a virtual environment based on a first set of views of portions of the virtual environment rendered at the user interface,
   wherein the first task comprises a first navigation task comprising presenting an elevated view of a virtual landscape that includes an internal course and obstacles and requiring the individual to control a guidable element via the at least one input device from an initial point on the internal course to a target point on the internal course and avoid the obstacles;
   generate a first set of data based on measurements of a first set of one or more parameters associated with allocentric navigation performed by the individual in response to the first task;
   render a second task at the user interface, wherein the second task requires the individual to rely on egocentric navigation capabilities to navigate in the virtual environment based on a second set of views of portions of the virtual environment rendered at the user interface,
   wherein the second task comprises a second navigation task comprising presenting a localized view of the virtual landscape that includes the internal course and the obstacles and requiring the individual to control the guidable element via the at least one input device from the initial point on the internal course to the target point on the internal course and avoid the obstacles without benefit of an aerial view of the entire course or a specified portion of the course;
   generate a second set of data based on measurements of a second set of one or more parameters associated with egocentric navigation performed by the individual in response to the second task;
   analyze the first set of data and the second set of data to generate an output of a quantitative metric of the individual's performance at the first task and the second task,
   wherein the quantitative metric comprises a measure of a degree of optimization of a path navigated by the individual through the internal course;
   compare the first set of data and the second set of data to a plurality of performance data for a plurality of individuals in a known disease population, wherein the plurality of performance data comprises performance data for the first task and the second task for the plurality of individuals in the known disease population; and
   generate an indication of cognitive ability in the individual based on the quantitative metric and the comparison of the first set of data and the second set of data to the plurality of performance data for the plurality of individuals in the known disease population.

2. The apparatus of claim 1, wherein the one or more processing units are further configured to generate a scoring output indicative of one or more of: (i) a likelihood of onset of a neurodegenerative condition of the individual, or (ii) a stage of progression of the neurodegenerative condition, based at least in part on the analysis of the first set of data and the second set of data.

3. The apparatus of claim 1, wherein the one or more processing units are further configured to generate a scoring output indicative of a relative health or strength of the caudate nucleus region of the brain of the individual relative to the entorhinal cortex and hippocampal regions of the brain of the individual, based at least in part on the analysis of the first and second sets of data.

4. The apparatus of claim 1, wherein the first task or the second task comprises one or more of a way-finding task, a path-plotting task, a seek task, a search and recovery task, or a direction-giving task.

5. The apparatus of claim 1, wherein the first set or the second set of one or more parameters comprises at least one of a measure of a navigation speed relative to the virtual environment, an orientation relative to the virtual environment, a velocity relative to the virtual environment, a choice of navigation strategy, a measure of a wait or delay period or a period of inaction during navigation, a time interval to complete a course, or a degree of optimization of a navigation path through a course.

6. The apparatus of claim 5, wherein the first set of one or more parameters comprise at least one of a measure of the individual's judgment about relative spatial positions between two points as determined based on distances relative to other objects in the virtual environment, a measure of the individual's ability to plot a novel course through a portion of the virtual environment that was previously known to the individual, or a measure of the individual's ability to spatially transform three or more memorized positions in the virtual environment arranged to cover two or more dimensions.

7. The apparatus of claim 5, wherein the second set of one or more parameters comprise at least one of a direction of the individual's movement relative to the virtual environment, a speed of the individual's movement relative to the virtual environment, a measure of the individual's memory of landmarks, a measure of the individual's memory of turn-by-turn directions, or a frequency or number of times of referral to an aerial or elevated view of a view.

8. An apparatus for enhancing one or more cognitive skills in an individual, said apparatus comprising:
a user interface comprising a display and at least one input device;
a memory to store processor-executable instructions; and
one or more processing units communicatively coupled to the user interface and the memory, wherein upon execution of the processor-executable instructions by the one or more processing units, the one or more processing units are configured to:
iteratively perform, in a series of at least two iterations, rendering at least two tasks that require an individual to navigate in a virtual environment based on one or more views of at least a portion of the virtual environment rendered at the user interface, in which the one or more views are automatically updated at the user interface as the individual navigates the virtual environment;
receiving navigation commands from the individual via the at least one input device in response to the at least two tasks;
controlling navigation in the virtual environment based on the received navigation commands;
measuring a first set of one or more parameters that provide information indicating the individual's allocentric navigation capabilities in performing the at least two tasks based on one or more first views of at least a portion of the virtual environment, and generating a first set of data having information about the measurements of the first set of one or more parameters,
wherein a first task in the at least two tasks comprises a first navigation task comprising presenting an elevated view of a virtual landscape that includes an internal course and obstacles and requiring the individual to control a guidable element via the at least one input device from an initial point on an internal course to a target point on the internal course and avoid the obstacles;
measuring a second set of one or more parameters that provide information indicating the individual's egocentric navigation capabilities in performing the tasks based on one or more second views of at least a portion of the virtual environment, and generating a second set of data having information about the measurements of the second set of one or more parameters,
wherein a second task in the at least two tasks comprises a second navigation task comprising presenting a localized view of the virtual landscape that includes the internal course and the obstacles and requiring the individual to control the guidable element via the at least one input device from the initial point on the internal course to the target point on the internal course and avoid the obstacles without benefit of an aerial view of the entire course or a specified portion of the course;
analyzing at least a portion of the first set of data and the second set of data to generate an output of a quantitative metric of the individual's performance at the first task and the second task,
wherein the quantitative metric comprises a measure of a degree of optimization of a path navigated by the individual through the internal course;
comparing the first set of data and the second set of data to a plurality of performance data for a plurality of individuals in a known disease population, wherein the plurality of performance data comprises performance data for the first task and the second task for the plurality of individuals in the known disease population; and
generating an indication of cognitive ability in the individual based on the quantitative metric and the comparison of the first set of data and the second set of data to the plurality of performance data for the plurality of individuals in the known disease population.

9. The apparatus of claim 8, wherein a task rendered in a second iteration or a later iteration is determined based at least in part on the analysis of at least one of the first set of data and the second set of data associated with one or more parameters measured in one or more previous iterations.

10. The apparatus of claim 8, wherein the one or more processing units are further configured to generate a scoring output indicative of one or more of: (i) a likelihood of onset of a neurodegenerative condition of the individual, or (ii) a stage of progression of the neurodegenerative condition, based at least in part on the analysis of at least one of the first set of data and the second set of data.

11. The apparatus of claim 8, wherein the one or more processing units are further configured to generate a scoring output indicative of a relative health or strength of the caudate nucleus region of the brain of the individual relative to the entorhinal cortex and hippocampal regions of the brain of the individual, based at least in part on the analysis of the at least a portion of the first set of data and the second set of data.

12. The apparatus of claim 8, wherein analyzing the at least a portion of the first set of data comprises analyzing the first set of data to provide a measure of the individual's performance at allocentric navigation.

13. The apparatus of claim 8, wherein analyzing the at least a portion of the second set of data comprises analyzing the second set of data to provide a measure of the individual's performance at egocentric navigation.

14. The apparatus of claim 8, wherein the first task or the second task comprises one or more of a way-finding task, a path-plotting task, a seek task, a search and recovery task, or a direction-giving task.

15. The apparatus of claim 8, wherein the first set or the second set of one or more parameters comprises at least one of a measure of a navigation speed relative to the virtual environment, an orientation relative to the virtual environment, a velocity relative to the virtual environment, a choice of navigation strategy, a measure of a wait or delay period or a period of inaction during navigation, a time interval to complete a course, or a degree of optimization of a navigation path through a course.

16. The apparatus of claim 15, wherein the first set of one or more parameters comprise at least one of a measure of the individual's judgment about relative spatial positions between two points as determined based on distances relative to other objects in the virtual environment, a measure of the individual's ability to plot a novel course through a portion of the virtual environment that was previously known to the individual, or a measure of the individual's ability to spatially transform three or more memorized positions in the virtual environment arranged to cover two or more dimensions.

17. The apparatus of claim 15, wherein the second set of one or more parameters comprise at least one of a direction of the individual's movement relative to the virtual environment, a speed of the individual's movement relative to the virtual environment, a measure of the individual's memory of landmarks, a measure of the individual's memory of turn-by-turn directions, or a frequency or number of times of referral to an aerial or elevated view of a view.

18. The apparatus of claim 8, wherein:
   prior to rendering the tasks at the user interface, the one or more processing units are configured to receive data indicative of one or more of an amount, concentration, or dose titration of a pharmaceutical agent, drug, or biologic being or to be administered to the individual and at least one classified data set associated with the plurality of individuals in the known disease population; and
   based at least in part on the analysis, generate an output to the user interface indicative of a change in the individual's cognitive ability.

19. The apparatus of claim 8, wherein the apparatus comprises one or more sensor components, and wherein the one or more processing units are configured to control the one or more sensor components to measure data indicative of the first set of one or more parameters and indicative of the second set of one or more parameters.

20. A system for generating an assessment of one or more cognitive skills in an individual, said system comprising:
   a user interface comprising a display and at least one input device;
   a memory to store processor-executable instructions; and
   one or more processing units communicatively engaged with the user interface and the memory, wherein upon execution of the processor-executable instructions by the one or more processing units, the one or more processing units are configured to:
   render a first task at the user interface, wherein the first task requires an individual to rely on allocentric navigation capabilities to navigate in a virtual environment based on a first set of views of portions of the virtual environment rendered at the user interface,
   wherein the first task comprises a first navigation task comprising presenting an elevated view of a virtual landscape that includes an internal course and obstacles and requiring the individual to control a guidable element via the at least one input device from an initial point on the internal course to a target point on the internal course and avoid the obstacles;
   generate a first set of data based on measurements of a first set of one or more parameters associated with allocentric navigation performed by the individual in response to the first task;
   render a second task at the user interface, wherein the second task requires the individual to rely on egocentric navigation capabilities to navigate in the virtual environment based on a second set of views of portions of the virtual environment rendered at the user interface,
   wherein the second task comprises a second navigation task comprising presenting a localized view of the landscape that includes the internal course and the obstacles and requiring the individual to control the guidable element via the at least one input device from the initial point on the internal course to the target point on the internal course and avoid the obstacles without benefit of an aerial view of the entire course or a specified portion of the course;
   generate a second set of data based on measurements of a second set of one or more parameters associated with egocentric navigation performed by the individual in response to the second task;
   analyze the first set of data and the second set of data to generate an output of a quantitative metric of the individual's performance at the first task and the second task,
   wherein the quantitative metric comprises a measure of a degree of optimization of a path navigated by the individual through the internal course;
   compare the first set of data and the second set of data to a plurality of performance data for a plurality of classified individuals in a known disease population, wherein the plurality of performance data comprises performance data for the first task and the second task for the plurality of individuals in the known disease population; and
   generate an indication of cognitive ability in the individual based on the quantitative metric and the comparison of the first set of data and the second set of data to the plurality of performance data for the plurality of individuals in the known disease population.

* * * * *